United States Patent
Goto

(10) Patent No.: US 8,953,865 B2
(45) Date of Patent: Feb. 10, 2015

(54) MEDICAL IMAGE PROCESSING DEVICE AND MEDICAL IMAGE PROCESSING METHOD

(75) Inventor: Yoshihiro Goto, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 20 days.

(21) Appl. No.: 13/985,758

(22) PCT Filed: Feb. 29, 2012

(86) PCT No.: PCT/JP2012/055026
§ 371 (c)(1),
(2), (4) Date: Aug. 15, 2013

(87) PCT Pub. No.: WO2012/118109
PCT Pub. Date: Sep. 7, 2012

(65) Prior Publication Data
US 2013/0322727 A1 Dec. 5, 2013

(30) Foreign Application Priority Data

Mar. 3, 2011 (JP) ................................ 2011-045892
Sep. 5, 2011 (JP) ................................ 2011-192522
Sep. 5, 2011 (JP) ................................ 2011-192548

(51) Int. Cl.
G06K 9/00 (2006.01)
G06T 7/00 (2006.01)
(Continued)

(52) U.S. Cl.
CPC ............... *G06T 7/0012* (2013.01); *G06T 19/00* (2013.01); *G06T 1/0007* (2013.01);
(Continued)

(58) Field of Classification Search
None
See application file for complete search history.

(56) References Cited

U.S. PATENT DOCUMENTS 6,990,231 B2 * 1/2006 Goto ............................ 382/154
8,121,369 B2 * 2/2012 Yoshida ........................ 382/128
(Continued)

FOREIGN PATENT DOCUMENTS

| JP | 6-215153 | 8/1994 |
|---|---|---|
| JP | 2000-139870 | 5/2000 |
| JP | 2009-247505 | 10/2009 |

OTHER PUBLICATIONS

International Search Report in PCT/JP2012/055026, Apr. 17, 2012.

*Primary Examiner* — Shefali Goradia
(74) *Attorney, Agent, or Firm* — Cooper & Dunham LLP

(57) ABSTRACT

Provided is, for example, a medical image display device which automatically create and display an image suitable for radiographic image interpretation of interosseous tissue or a 3-dimensional image of a vertebral body separated one by one with high precision. A medical image processing device (1) creates a first conversion image (in step (S1)), extracts a first intervertebral disc region from the first conversion image (in step (S2)), and specifies two coordinates (P1, P2) from among the pixels included in the first intervertebral disc region (in step (S3)). Next, the medical image processing device (1) creates a second conversion image (in step (S4)), extracts a second intervertebral disc region (in step (S5)), and specifies two coordinates (Q1, Q2) from the second intervertebral disc region (in step (S6)). Next, the medical image processing device (1) calculates a reference curved surface including at least four feature points of the coordinates (P1, P2, Q1, Q2) on a per intervertebral disc basis and, based on the reference curved surface, creates a display image (in step (S7)), and displays the display image (in step (S8)).

17 Claims, 27 Drawing Sheets

(51) Int. Cl.
  *G06T 19/00* (2011.01)
  *G06T 1/00* (2006.01)
  *A61B 5/00* (2006.01)
  *A61B 5/055* (2006.01)
  *A61B 6/03* (2006.01)
  *A61B 6/00* (2006.01)
(52) U.S. Cl.
  CPC .............. *A61B 5/4514* (2013.01); *A61B 5/004* (2013.01); *A61B 5/055* (2013.01); *A61B 6/032* (2013.01); *A61B 6/505* (2013.01); *G06T 2219/008* (2013.01); *G06T 2210/41* (2013.01)
  USPC ........................................................ 382/132

(56) References Cited

U.S. PATENT DOCUMENTS

| | | | |
|---|---|---|---|
| 8,165,370 B2 * | 4/2012 | Inoue et al. | 382/128 |
| 2002/0176614 A1 * | 11/2002 | Kuth et al. | 382/128 |
| 2011/0164798 A1 | 7/2011 | Masumoto | |

* cited by examiner (a)

(b)

(a)

(b)

(a)

(b)

(a)

31c FIRST CONVERSION IMAGE (b)

30 CROSS-SECTIONAL IMAGE
31c FIRST CONVERSION IMAGE
33c SECOND CONVERSION IMAGE

FIG.18

211 STORAGE AREA (a)

| x-COORDINATE | y-COORDINATE | DISTANCE | DENSITY |
|---|---|---|---|
| x(1) | y(1) | r(1) | I(1) |
| x(2) | y(2) | r(2) | I(2) |
| x(3) | y(3) | r(3) | I(3) |
| ... | ... | ... | ... |
| x(N) | y(N) | r(N) | I(N) |

212 STORAGE AREA (b)

| r(1) | r(2) | r(3) | ... | r(N) |
|---|---|---|---|---|

MEDICAL IMAGE PROCESSING DEVICE AND MEDICAL IMAGE PROCESSING METHOD

FIELD OF THE INVENTION

The present invention relates to a medical image processing device, etc. that executes image processing of medical images such as CT images, MR images and US images. In particular, it relates to an image processing technique that creates and displays images suitable for radiographic image interpretation of intervertebral disc tissue, and the like.

DESCRIPTION OF RELATED ART

Medical diagnosis using CT (Computed Tomography) images, MR (Magnetic Resonance) images or US (Ultrasound) images has been made conventionally, and research and development of an image processing technique that creates and displays images appropriate for radiographic image interpretation of target tissue has also been carried out in recent years.

A method has been disclosed in Patent Document 1, in which an image display device selects and calls up, when a line ROI is set on a scanogram by an observer, a slice image (cross-sectional image) stored in storage means based on the positional information on the scanogram and displays the image on a display means.

Also, Patent Document 2 discloses a method of determining a slice plane of an intervertebral disc, in which a processing device creates an edge image, when a user specifies one point of an intervertebral edge portion, for determining a slice plane which includes an intervertebral disc and is parallel to the intervertebral disc.

PRIOR ART DOCUMENTS

Patent Documents

Patent Document 1: JP-A-H02-237548
Patent Document 2: JP-A-H07-51248
Patent Document 3: Japanese Patent No. 4393016
Patent Document 4: Japanese Patent No. 4169967

Non-Patent Document

Non-patent Document 1: Masahiro Uehara, Shinsuke Saita, Mitsuru Kubo, Yoshiki Kawata, Noboru Niki, Masako Ito, Hiromu Nishitani, Keigo Tominaga and Noriyuki Moriyama, A Computer Aided Diagnosis for Osteoporosis using Multi-slice CT Images, IEICE Technical Report MI2006-164(2007-1), p 25~28, 2007

SUMMARY OF INVENTION

Technical Problem

However, the techniques in Patent Document 1 and Patent Document 2 have a disadvantage that a user must confirm images each time necessary information (line ROI, intervertebral disc edge portion, etc.) is input.

Also, including other known techniques, a technique that automatically creates and displays images suitable for radiographic image interpretation of specified tissue between bones had not yet been developed.

Here, specified tissue existing between bones is, for example an intervertebral disc that is cartilage tissue between vertebrae, and cartilage tissue existing in knee joints, elbow joints, hip joints, and so on. Hereinafter, such specified tissue which exists between bones is referred to as "interosseous tissue".

Also, an image suitable for radiographical image interpretation of interrosseous tissue is, for example an image of which the condition in an entire interosseous tissue can be visibly identified.

Considering the above-described problem, the objective of the present invention is to provide a medical image display device, and the like capable of automatically creating and displaying an image suitable for radiographic image interpretation of interosseous tissue or a 3-dimensional image of a vertebral body separated one by one with high precision.

BRIEF SUMMARY OF THE INVENTION

In order to achieve the above-described objective, the first invention is a medical image processing device that creates a display image formed by the pixels of plural cross-sectional images, to be displayed on a display device for radiographic image interpretation of interosseous tissue or bone tissue, comprising:

a conversion image creation unit configured to create a conversion image including the interosseous tissue and plural bone tissues with the interosseious tissue therebetween on the basis of the plural cross-sectional images;

a feature point specification unit configured to execute processing which specifies at least two points as feature points by a predetermined specifying condition using at least two conversion images having different conversion curved surfaces indicating the position of the pixels that constitute the conversion image, for each of the conversion images;

a display image creation unit configured to calculate a reference curved surface for creating the display image on the basis of the feature points and creates the display image on the basis of the reference curved surface; and a display unit configured to display the display image on the display device.

The second invention is a medical image processing method of creating a display image formed by the pixels of plural cross-sectional images, to be displayed on a display device for radiographic image interpretation of interprosseous tissue or bone tissue, including:

creation of a composite image including the interosseous tissue and plural bone tissues having the interosseous tissue therebetween on the basis of the plural cross-sectional images;

specification of feature points by specifying at least two points as feature points by a predetermined specified condition using at least two conversion images having different conversion curved surfaces indicating the position of the pixels that constitute the conversion image, for each of the conversion images;

creation of a display image by calculating a reference curved surface for creating the display image on the basis of the feature points and creating the display image on the basis of the reference curved surface; and display of the display image on the display device.

Effect of the Invention

In accordance with the present invention, it is possible to provide a medical image display device, and the like capable of automatically creating and displaying an image suitable for radiographic image interpretation of interprosseous tissue or a 3-dimensional image of a vertebral body separated one by one with high precision.

DESCRIPTION OF REFERENCE NUMERALS

FIG. 18 is an example of a storage area in the first display image creating process.

DETAILED DESCRIPTION OF THE INVENTION

The present invention is a medical image processing device which creates a display image formed by the pixels of plural cross-sectional images to be displayed on a display device for radiographic image interpretation of interosseous tissue or bone tissue, comprising:

a conversion image creation unit configured to create a conversion image including the interosseous tissue and plural bone tissues having the interosseous tissue therebetween, on the basis of the plural cross-sectional images;

a feature point specification unit configured to execute a process that specifies at least two points as feature points by a predetermined specifying condition, using at least two conversion images having different conversion curved surfaces showing the positions of the pixels that constitute the conversion image, for each of the conversion images;

a display image creation unit configured to calculate a reference curved surface for creating the display image on the basis of the feature points and create the display image on the basis of the reference curved surface; and a display unit configured to display the display image on the display device.

An embodiment of the present invention will be described below in detail referring to the attached drawings.

First, configuration of an image processing system 1 to which a medical image processing device 1 of the present invention is applied will be described referring to FIG. 1.

Figure 1:
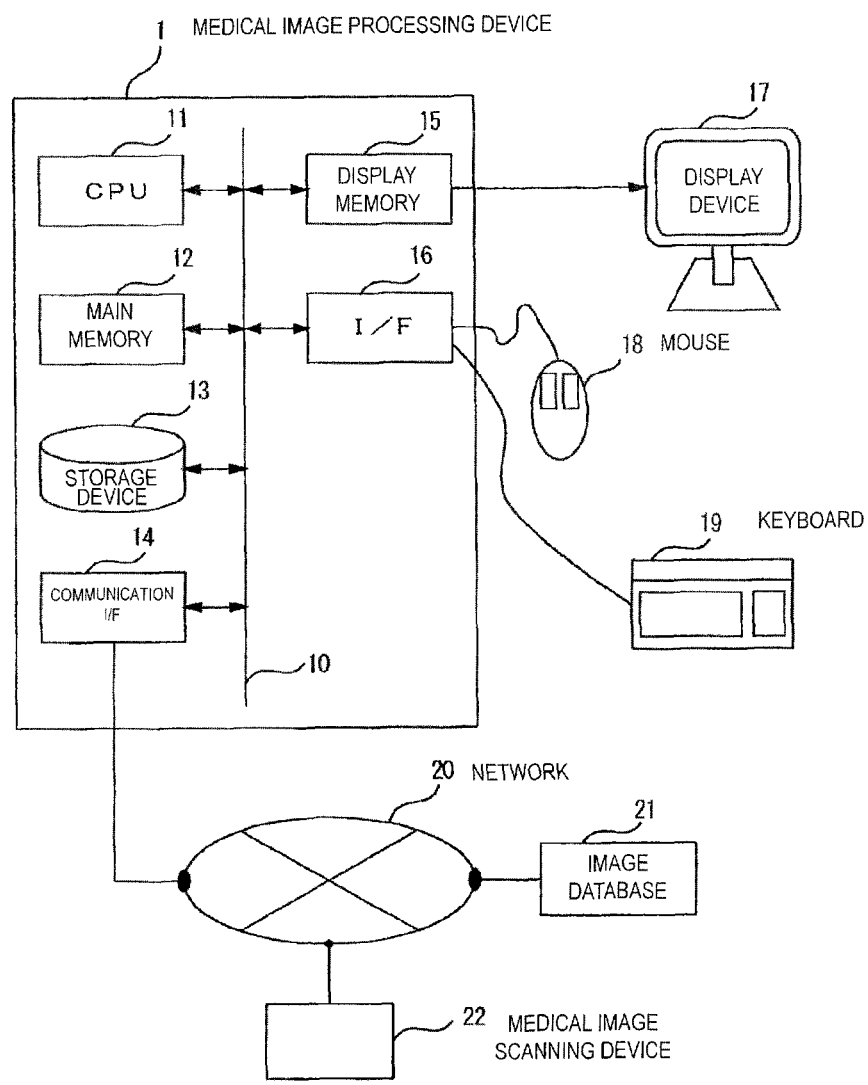
FIG. 1 shows hardware configuration of a medical image processing device.

As shown in FIG. 1, a display device 17 and input devices, etc. such as a mouse 18 and a keyboard 19 are connected to the medical image processing device 1. Also, an image database 21, a medical image scanning device 22, etc. may be connected to the medical image processing device 1 via a network 20.

The medical image processing device 1 is a computer for executing processing such as image generation and image analysis.

The medical image processing device 1 comprises, as shown in FIG. 1, a CPU (Central Processing Unit) 11, a main memory 12, a storage device 13, a communication interface (communication I/F) 14, a display memory 15, an interface (I/F) 16 for external devices such as a mouse 18 and a keyboard 19, and the respective components are connected via a bus 10.

The CPU 11 calls up the program stored in the main memory 12 or a storage device 13, etc. to a work memory area on a RAM in the main memory 12, performs drive control of the respective components connected to each other via the bus 10, and carries out various processing to be executed by the medical image processing device 1.

The main memory 12 is formed by devices such as a ROM (Read Only Memory) and a RAM (Random Access Memory). The ROM keeps a boot program of a computer or a program, data, etc. of BIOS, and the like on a permanent basis. Also, the RAM keeps a program, data, and so on loaded from the ROM, the storage device 13, etc. on a temporary basis, and comprises a work area to be used by the CPU 11 for performing various processing.

The storage device 13 performs reading and writing of data for an HDD (hard disc drive) or other recording media, and stores a program to be executed by the CPU 11, and data, OS (operating system), etc. necessary for executing the program. The program to be stored is a control program which is equivalent to OS or application program. These respective program codes are read out as needed by the CPU 11, transferred to the RAM in the main memory 12, and carried out as various means.

The communication I/F 14 has devices such as a communication control device and a communication port, and mediates communication between the medical image processing device 1 and the network 20. Also, the communication I/F 14 controls communication with an image database 21, another computer, or a medical image scanning device 22 such as an X-ray CT apparatus and an MRI apparatus via the network 20.

The I/F 16 is a port for connecting peripheral devices, and performs transmission and reception of data between the peripheral devices.

The display memory 15 is a buffer which temporarily accumulates the display data input from CPU 11. The accumulated display data is output to the display device 17 at a predetermined timing.

The display device 17 is configured by a liquid crystal panel, a display device such as a CRT monitor, and a logic circuit for performing display processing in coordination with the display device, and is connected to the CPU 11 via the display memory 15. The display device 17 displays the display data accumulated in the display memory 15 under control of the CPU 11.

The mouse 18 and the keyboard 19 output various commands or information input by an operator to the CPU 11. The operator interactively operates the medical image processing device 1 using external devices such as the mouse 18 and the keyboard 19.

The display device 17 and input devices (the mouse 18 and the keyboard 19) may also be integrated like, for example a display with a touch panel. In this case, keyboard arrangement of the keyboard 19 may also be displayed on the display with a touch panel.

The network 20 includes various communication network such as a LAN (Local Area Network), WAN (Wide Area Network), intranet and Internet, and mediates communication connection between the image database 21 or other information equipment, and the medical image processing device 1.

The image database 21 accumulates and stores the image data scanned by the medical image scanning device 22. While the image database 21 is connected to the medical image processing device 1 via the network 20 in the example of FIG. 1, the image database 21 may also be provided, for example in the storage device 13 of the medical image processing device 1.

Embodiment 1

Next, Embodiment 1 will be described referring to FIG. 2~FIG. 5. The medical image processing device 1 in Embodiment 1 creates and displays, in particular, a 2-dimensional image suitable for radiographic image interpretation of an intervertebral disc, and the like.

First, a display image creating process will be described referring to FIG. 2~FIG. 5. In FIG. 2~FIG. 5, an intervertebral disc which is cartilage tissue that exists between vertebrae will be described as an example of interosseous tissue. Also, a CT image is described as an example of a medical image.

A "display image" in Embodiment 1 is an image to be displayed on the display device 17 for radiographic image interpretation of interosseous tissue, formed by the pixels of plural cross-sectional images. For example, in a case of a CT image, an MPR (Multi Planer Reconstruction) image, etc. obtained by extracting an arbitrary cross-section of 3-dimensionally collected CT value information is the image formed by the pixels of plural cross-sectional images. The display image in Embodiment 1, which is different from a mere MPR image, is generated by calculating a curved surface in accordance with the shape of interosseous tissue and extracting the pixels from plural cross-sectional images on the basis of a calculated curved surface. Hereinafter, the curved surface indicating the position of the pixels which constitute a display image is referred to as a "display curved surface".

Figure 2:
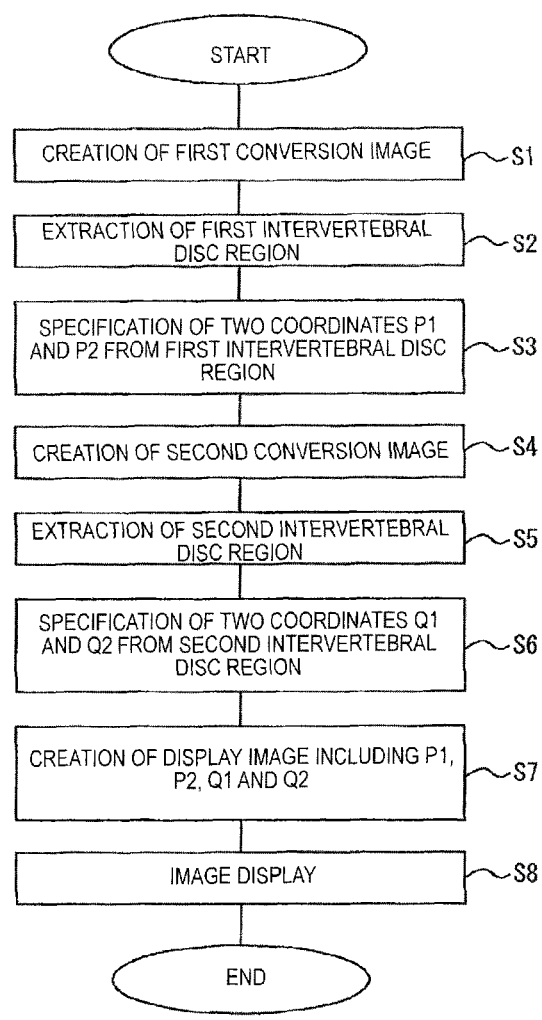
FIG. 2 is a flowchart showing the flow of the display image creation process in Embodiment 1.

As shown in FIG. 2, the CPU 11 of the medical image processing device 1 generates a first conversion image (step S1). Here, a conversion image is an image including an intervertebral disc (interosseous tissue) and plural vertebrae (bone tissue) having an intervertebral disc (interosseous tissue) therebetween, and is an MPH image based on plural cross-sectional images in the case of a CT image. The conversion image is created for specifying feature points of a display curved surface. When an intervertebral disc is thin, enlarging the image in the body-axis direction of an object makes it easier to perform sequential processing by the CPU 11.

Figure 3:
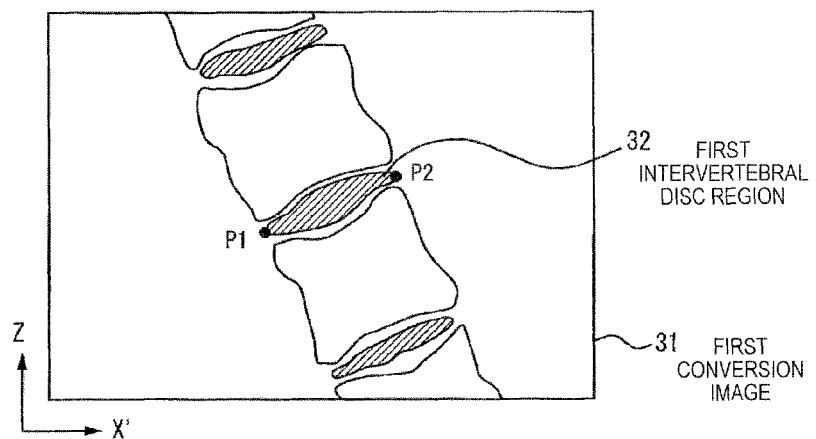
FIG. 3 is a view for explaining an example of a conversion image.
Figure 3:
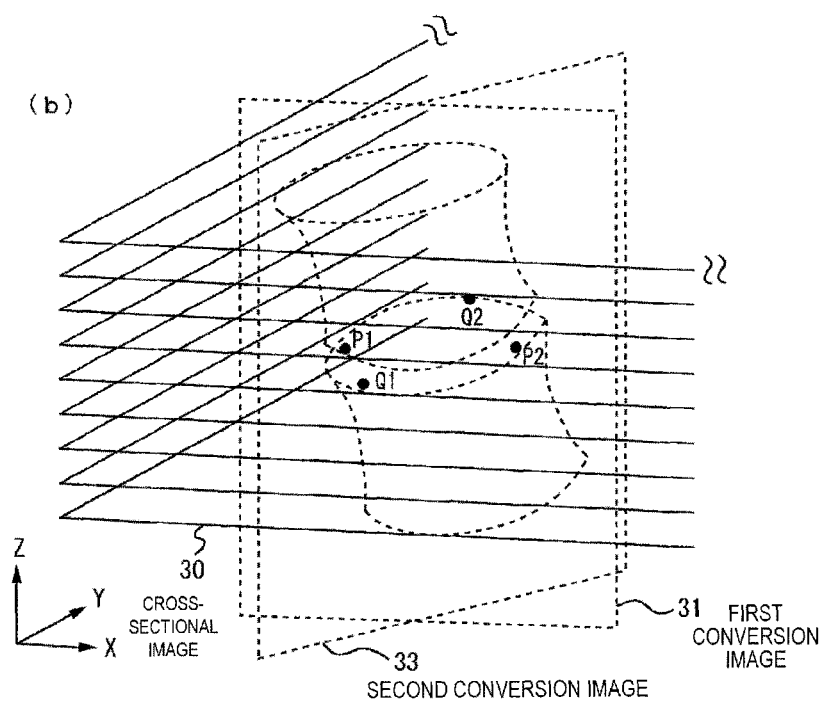

FIG. 3(*a*) shows an example of the first conversion image. When the body-axis direction of the object is set as the Z-axis and the coordinate axes of the cross-sectional image are set as the X-axis and the Y-axis, the coordinate axes of the first conversion image 31 are set, for example as X'-axis and Z-axis. In other words, the first conversion image 31 shown in FIG. 3(*a*) is the image cut out by setting a plane which extends in the Z-axis direction as a cut cross-section. As shown in FIG. 3(*a*), the first conversion image 31 includes intervertebral discs and plural bone regions having the intervertebral disc therebetween.

Next, the CPU 11 extracts a first intervertebral disc region from the first conversion image (step S2). The intervertebral disc region is an assembly of the pixels showing the intervertebral disc. In FIG. 3(*a*), a shaded area indicates the intervertebral disc region. The intervertebral disc areas are also indicated by a shaded area in other drawings. Since there are plural intervertebral discs, the CPU 11 always specifies one intervertebral disc as a processing target, then executes the sequential processing.

In FIG. 3(*a*), the second intervertebral disc from the top is indicated as a processing target among the intervertebral discs included in the first conversion image 31, and is set as a first intervertebral disc region 32.

The CPU 11 binarizes the first conversion image by, for example the threshold value processing, and extracts the first intervertebral disc region. The CPU 11 can also apply, for example the abnormal shade extraction method disclosed in Patent Document 3 to the extraction of an intervertebral disc. Also, the CPU 11 can apply, for example the region discrimination method disclosed in Patent Document 4 to the extraction of an intervertebral disc.

Next, the CPU 11 specifies two coordinates P1 and P2 from among the pixels included in the first intevertebral disc region (step S3). The CPU 11 specifies, for example two points that are farthest away from each other within the first intervertebral disc region as coordinates P1 and P2. In other words, the CPU 11 calculates the distance between two arbitrary points which form the contour of the first intervertebral disc region, and specifies the two points which are most apart from each other as coordinates P1 and P2. The coordinates P1 and P2 are used as feature points for determining a display curved surface in the process of S7.

In FIG. 3(*a*), coordinates P1 and P2 are indicated at both edges in the longitudinal direction of the first intervertebral disc region 32.

Next, as in steps S1~S3, the CPU 11 creates a second conversion image (step S4), extracts a second intervertebral disc region (step S5), and specifies two coordinates Q1 and Q2 from the second intervertebral disc region (step S6). Here, the CPU 11 creates the second conversion image so that the conversion curved surfaces are differentiated between the first conversion image and the second conversion image. A conversion curved surface is a curved surface which indicates the position of the pixels that constitute the conversion image. Also, coordinates Q1 and Q2 are used as feature points for determining a display curved surface in the process of step S7.

FIG. 3(b) indicates that the first conversion image 31 and the second conversion image 32 are created on the basis of plural cross-sectional images 30. It also shows that the conversion curved surfaces (flat surfaces in FIG. 3(b)) of the first conversion image 31 and the second conversion image 32 are differentiated from each other. Also, coordinates P1, P2 Q1 and Q2 are indicated as four feature points for determining a display curved surface.

While the conversion curved surfaces of the first conversion image 31 and the second conversion image 32 are presented as flat surfaces in FIG. 3(b), they may generally be presented as curved surfaces. For example, the CPU 11 may also determine a conversion curved surface to fit backbones, for creating the first conversion image 31 and the second conversion image 32 that are cut out by the conversion curved surfaces.

As shown in step S1~step 6, the CPU 11 repeats plural times the process of specifying at least two points as feature points for determining a display curved surface, by a predetermined specifying condition (for example, condition to specify two points which are most apart from each other within an intervertebral disc region) on the basis of the conversion images. In concrete terms, the process is to be repeated at least two times using the conversion images having different conversion curved surfaces. The number of feature points does not have to be limited to four, and five or more feature points may also be used.

Figure 4:
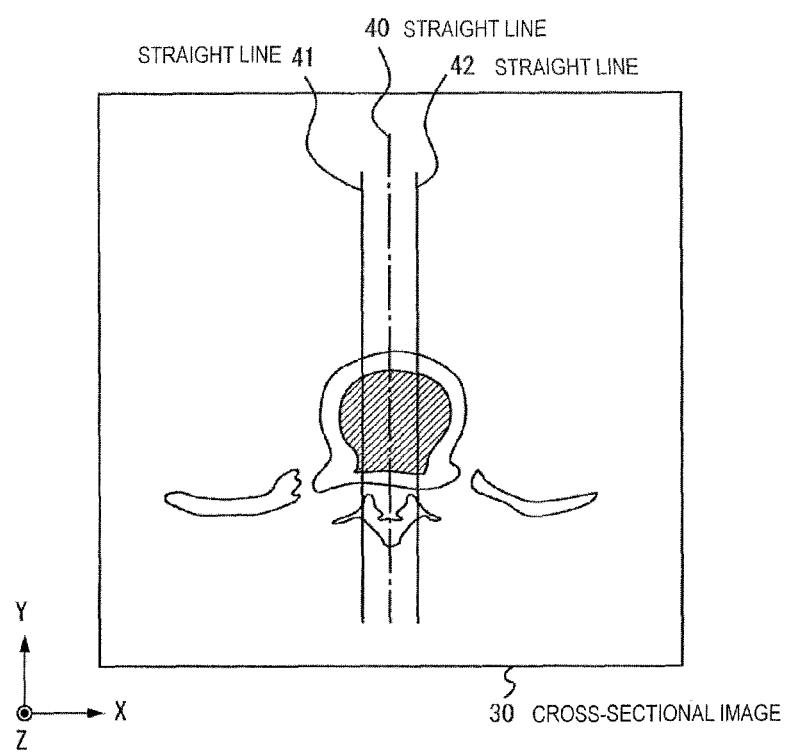
FIG. 4 is a view for explaining an example of a process for determining a conversion curved surface.

FIG. 4 shows an example of the method for determining a conversion curved surface of a conversion image. In the method shown in FIG. 4, the CPU 11 sets the straight line including the most pixels of the vertebra from among the straight lines extended in one axis direction of an intervertebral disc region in a cross-sectional image as the center line, and calculates the curved surface including the straight lines parallel to the center line as a conversion curved surface.

First, the CPU 11 extracts the center line which extends in the Y-axis direction (one axis-direction of an intervertebral disc region in a cross-sectional image). The CPU 11 calculates, as an X-coordinate position of the center line, for example the X-coordinate position having the greatest ratio of existing bone in the Y-direction or an X-coordinate position which gives the minimum point of the Y-coordinate among the pixels showing a vertebra. The CPU 11 extracts the center line on the basis of the calculated X-coordinate position. In FIG. 4, a straight line 40 is the center line.

Next, the CPU 11 extracts two straight lines that are parallel to the straight line 40 which is the center line. In FIG. 4, a straight line 41 and a straight line 42 are the straight lines parallel to the center line. The CPU 11 calculates, as the X-coordinate position of the parallel straight line, for example the X-coordinate position which divides the X-coordinate direction width of a one-side region (the left-side region or the right-side region) of the center line internally by a predetermined ratio or the X-coordinate position which divides the area of a one-side region of the center line internally by a predetermined ratio. The CPU 11 extracts a parallel straight line on the basis of the calculated X-coordinate position.

Then the CPU 11 creates the first conversion image which includes, for example the straight line 41, and has the plane orthogonal to the X-axis as the conversion curved surface. Also, the CPU 11 creates the second conversion image which includes, for example the straight line 42 and has the plane orthogonal to the X-axis as the conversion curved surface.

Conversion curved surfaces in a conversion image are not limited to be parallel to each other, and they also may cross each other as shown in FIG. 3(b). Also, as previously mentioned, the conversion curved surfaces of a conversion image may be not only flat surfaces, but also curved surfaces.

The number of conversion images may be not only two but also three or more. In an example shown in FIG. 4, the CPU 11 may create a conversion image of an area, for example ranging from the straight line 41 to the straight line 42 via the straight line 40. In this case, the CPU 11 can display the conversion image continuously on the display device 17.

The explanation of the flowchart in FIG. 2 will now be continued.

The CPU 11 creates a display image by calculating a display curved surface including at least four feature points of coordinates P1, P2, Q1 and Q2 for each intervertebral disc and extracting the pixel values corresponding to the pixels of the display curved surface from the plural cross-sectional images (step S7), and displays the display image on the display device 17 (step S8).

Figure 5:
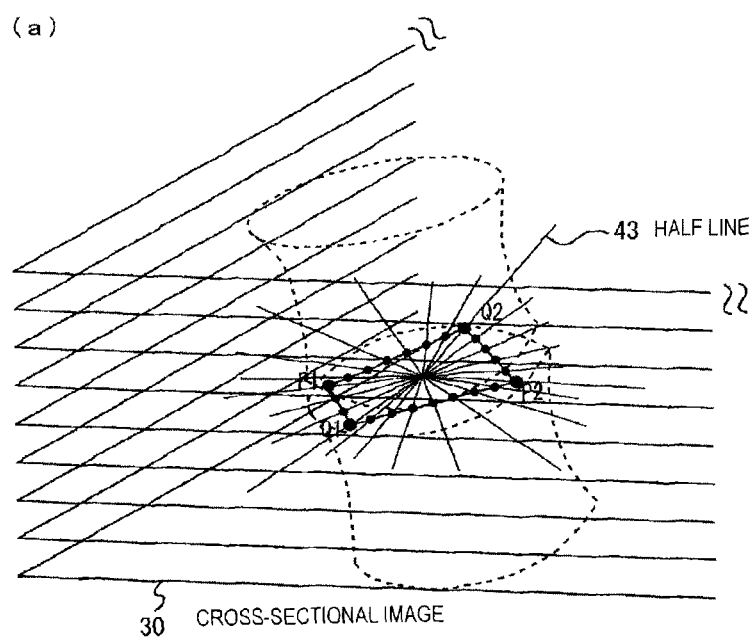
FIG. 5 is a view for explaining a process for calculating a display curved surface.
Figure 5:
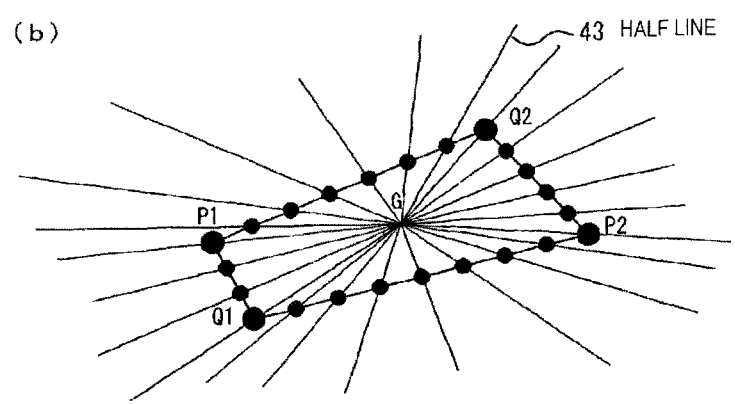

FIG. 5 shows an example of a method of calculating a display curved surface. In the method shown in FIG. 5, the CPU 11 sets the assembly of half lines which pass through the sampling points on the line segment having the feature points as their edge points and has the barycenter of the feature points as their edge point, as a display curved surface.

In FIG. 5(a), the assembly of half lines 43 is indicated to correspond to FIG. 3(b). In FIG. 5(b), a part of FIG. 5(a) is enlarged to show the assembly of the half lines 43.

First, the CPU 11 extracts the line segment having four feature points of P1, P2, Q1 and Q2 as its edge points. In concrete terms, the CPU 11 extracts four line segments, i.e. a line segment having edge points of P1 and Q1, a line segment having edge points of Q1 and P2, a line segment having edge points of P2 and Q2 and a line segment having edge points of Q2 and P1.

Next, the CPU 11 calculates the sampling points on the four line segments. The sampling interval is, for example the same as or a half of the pixel interval.

Next, the CPU 11 calculates barycenter G of the four feature points P1, P2, Q1 and Q2.

Then the CPU 11 calculates the half lines having barycenter G as their edge point and passing through the respective sampling points, and sets the assembly of half lines as a display curved surface.

It is preferable that the CPU 11 extracts the line segments so that barycenter G is encompassed by four line segments when viewed from any direction, as shown in FIG. 5. In other words, it is preferable to extract the four line segments so that the quadrilateral having the four segments as each of its sides becomes a convex quadrilateral when viewed from an arbitrary direction (so that each inner angle is less than 180 degrees).

The method of determining display curved surface is not limited to the example shown in FIG. 5. For example, the CPU 11 may also calculate the equation of a curved surface which is approximated by four feature points using the method such as least square. Also as the modification of the example shown in FIG. 5, the CPU 11 may calculate four spline curves in place of four line segments, and set the assembly of the half lines which pass through the sampling points on the spline curve lines and has the barycenter of feature point as their end point as a display curved surface.

The display image created according to the above-described procedure is the image in which the condition of an entire intervertebral disc can be visually identified and is suitable for radiographic image interpretation thereof.

The method for fine adjustment of the position and inclination of a display image which is displayed on the display device 17 will be described below referring to FIG. 6~FIG. 12. In FIG. 6~FIG. 12, an intervertebral disc which is cartilage tissue exists between vertebrae is described as an example of interosseous tissue.

Since the position and inclination of a display image are determined by the position and inclination of the display curved surface, the CPU 11 inputs the command information for translating the display curved surface or for changing the inclination of the display curved surface from the input device, thereby recreating the display image in accordance with the command information. Then the CPU 11 updates and displays the display image which is displayed on the display device 17.

Figure 6:
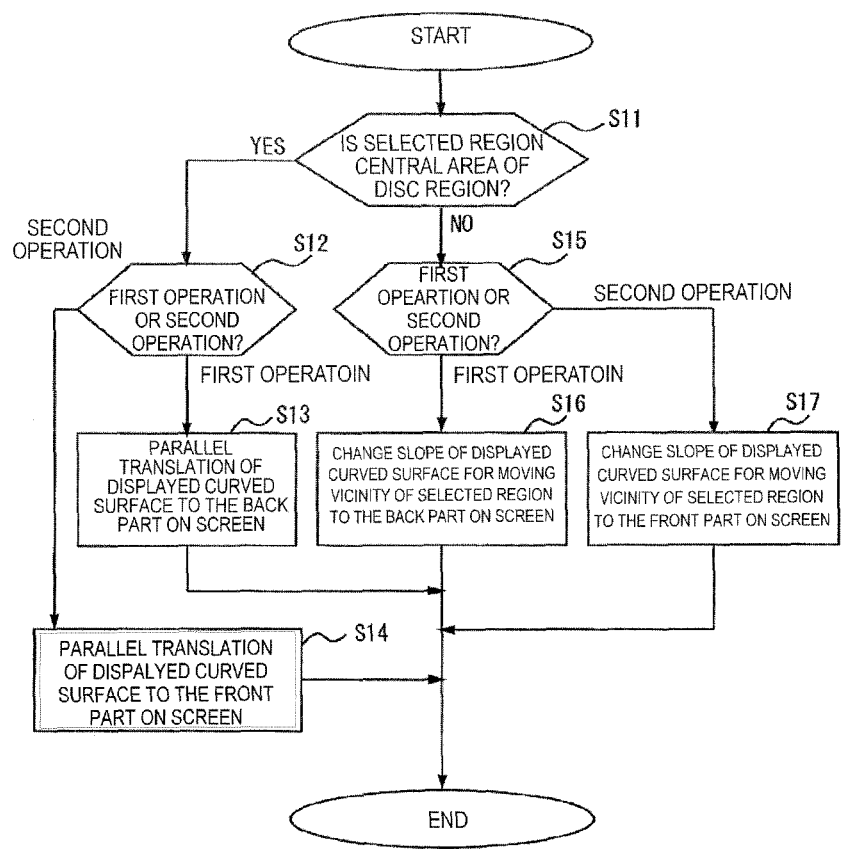
FIG. 6 is a flowchart showing the flow of a process for updating a display image.

FIG. 6 shows the flow of processing which makes fine adjustment of the position or inclination of the display image which is displayed on the display device 17 by the command issued by a user. In the example shown in FIG. 6, the CPU 11 executes one of four commands: (1) to translate the display curved surface in a first direction, (2) to translate the display curved surface in a second direction which is different from the first direction, (3) to tilt the display curved surface in a first direction, or (4) to tilt the display curved surface in a second direction which is different from the first direction.

When the user selects a part of the screen by an input device (for example, the mouse 18), the CPU 11 confirms whether or not the selected region is near the center of the intervertebral disc, as shown in FIG. 6 (step S11).

When the selected region is near the center (YES in step S11), the CPU 11 carries out step S12. When it is not near the center, i.e. when the selected region is in the vicinity of the intervertebral region, step S15 is carried out.

In step S12, the CPU 11 confirms whether the operation used at the time that the region was selected is a first operation or a second operation. For example, when an input device is the mouse 18, the first operation is "one click" and the second operation is "double click".

If the operation is the first operation ("first operation" in step S12), the CPU 11 translates the display curved surface toward the back of the screen (step S13).

If the operation is the second operation ("second operation" in step S12), the CPU 11 translates the display curved surface toward the front of the screen (step S14).

In step S15, the CPU 11 confirms if the operation used at the time that the region was selected is the first operation or the second operation.

If the operation is the first operation ("first operation" in step S15), the CPU 11 changes the inclination of the display curve surface so that the vicinity of the selected region moves toward the back of the screen (step S16).

If the operation is the second operation ("second operation" in step S12), the CPU 11 changes the inclination of the display curved surface so that the vicinity of the selected region moves toward the front of the screen (step S17).

In any case of steps S13, S14, S16 and S17, the CPU 11 recreates the display image on the basis of the changed display curved surface, updates and displays the display image which is displayed on the display device 17.

Figure 7:
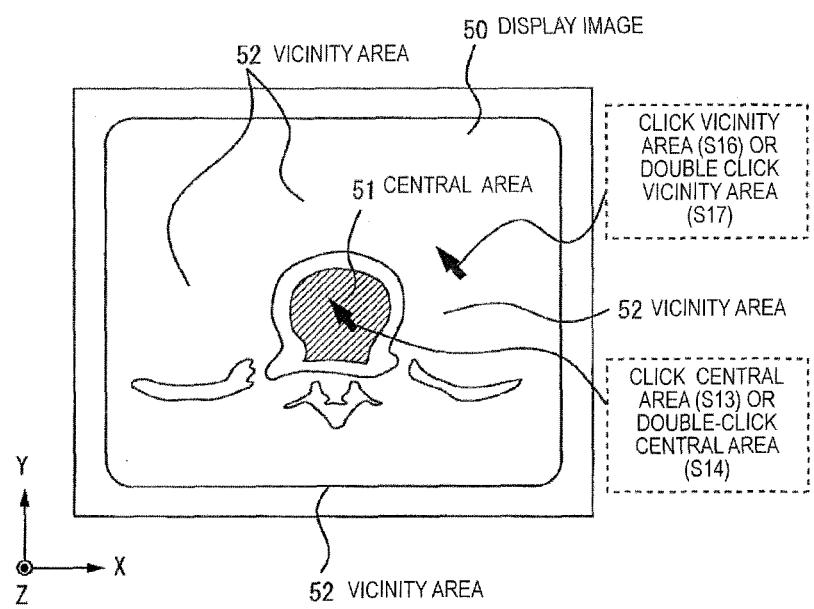
FIG. 7 is a first screen example for commanding movement of a display curved surface.
Figure 7:
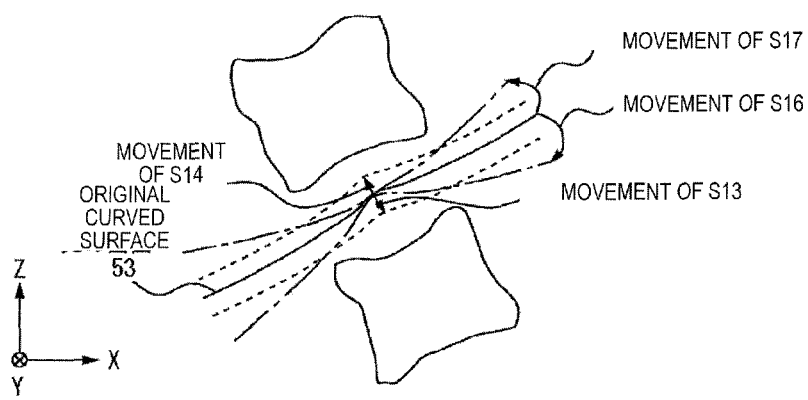

FIG. 7 schematically shows the four commands indicated in FIG. 6. As shown in FIG. 7($a$), the CPU 11 divides the region in a display image 50 into a central area 51 of an intervertebral disc region (shaded area in FIG. 7) and vicinity areas 52.

Then the CPU 11 identifies that one input operation has performed from among: (1) clicking of the central area 51 by an operator using the mouse 18 (S13); (2) double-clicking of the central area 51 by a user using the use 18 (S14); (3) clicking the vicinity area 52 by an operator using the mouse 18 (S16) and (4) double-clicking the vicinity area 52 by an operator using the mouse 18 (S17). In accordance with the identified input operation, the CPU 11 determines whether the change should be made on the translation or the inclination, and also determines the direction of the translation or the inclination, so as to change the position or the inclination of the display curved surface.

FIG. 7($b$) shows the movement of the display curved surface by the mouse position (denoted by solid black arrows) in FIG. 7($a$). As shown in FIG. 7($b$), the mouse position is translated by a predetermined distance in a negative direction approximately along the Z-axis (body axis) in step S13. A predetermined distance here is, for example 0.5 pixel or one pixel. In the movement of step S14, the mouse position is translated by a predetermined distance in a positive direction approximately along the Z-axis (body-axis direction). In the movement of step S16, the mouse position is rotationally-transferred by a predetermined distance clockwise based on the barycenter of the display curved surface. In the movement of step S17, the mouse position is rotationally-transferred by a predetermined distance counterclockwise based on the barycenter of the display curved surface.

Figure 8:
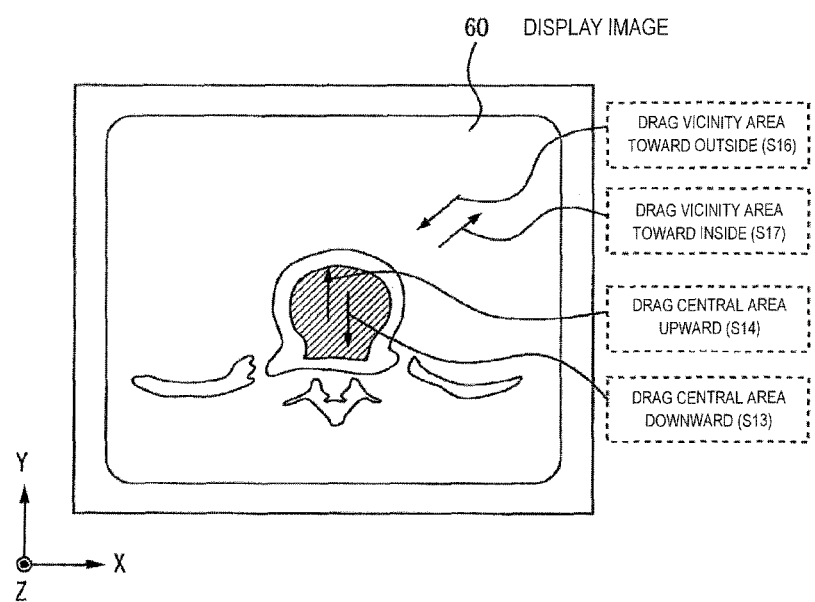
FIG. 8 is a second screen example for commanding movement of a display curved surface.

FIG. 8 shows the modification of the first operation and the second operation. That is, the first operation and the second operation are performed, in place of single click and double click, by dragging in a first direction and dragging in a direction which is 180 degrees opposite from the first direction.

As shown in FIG. 8, the CPU 11 divides the region of a display image 60 into the central area of an intervertebral disc region (the shaded area in FIG. 8) and the vicinity area.

Then CPU 11 identifies that one input operation has been carried out from among: (1) downward dragging of the central area by an operator using the mouse 18 (S13); (2) upward dragging of the central area by an operator using the mouse 18 (S14); (3) dragging of the vicinity area toward the outside by an operator using the mouse 18 (S16) and (4) dragging of the vicinity area toward the inside by an operator using the mouse 18 (S17). In accordance with the identified input operation, the CPU 11 determines whether the change should be made on the translation or the inclination, and also determines the direction of the translation or the inclination, so as to change the position or the inclination of the display curved surface.

As shown in FIG. 7 and FIG. 8, the CPU 11 translates the display curved surface toward the back of the screen when the central area of the intervertebral disc region is selected by the first operation in the display image displayed on the display device 17, and translates the display curved surface toward the front of the screen when the central area is selected by the second operation which is different from the first operation. The CPU 11 changes the inclination of the display curved surface when the vicinity area of the intervertebral disc region is selected by the first operation in the display image displayed in the display device so that the selected vicinity area moves toward the back of the screen, and changes the inclination of the display curved surface when the vicinity area is selected by the second operation so that the vicinity of the selected region moves toward the front of the screen.

In addition, the previously described central area in the intervertebral disc region may be set as the central area of the display image.

As for the command information regarding the change of the inclination of a display curved surface, it may be set so that the angle of the inclination increases as the selected place gets farther away from the central area.

Figure 9:
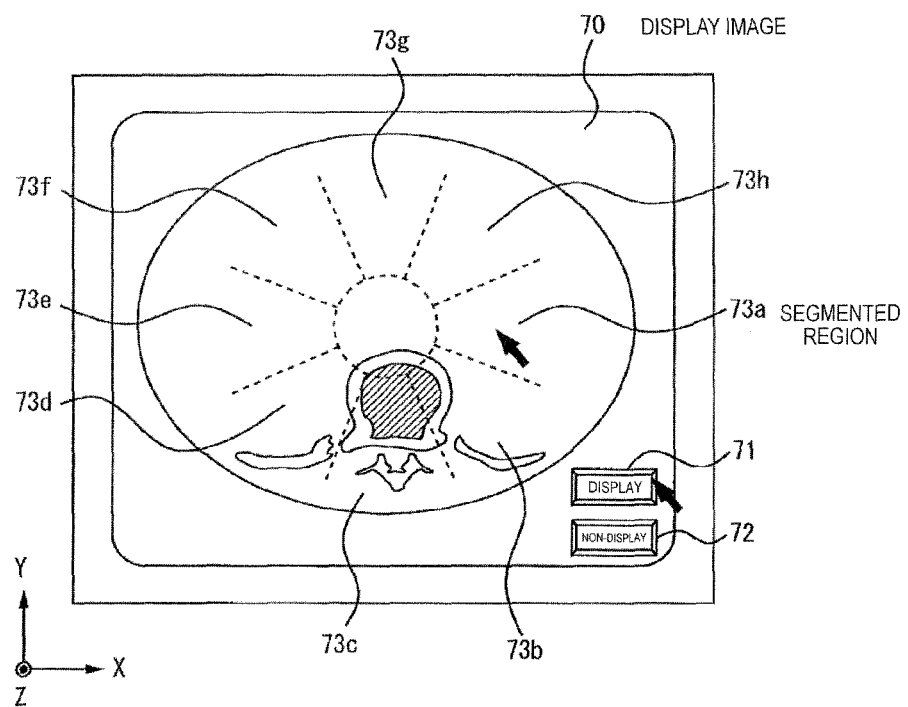
FIG. 9 is a third screen example for commanding movement of a display curved surface.

In FIG. 9, segmented regions 73a~73h for segmenting a display image 70 are indicated so that the user can easily identify the position to be tilted at the time of giving a command to change the inclination of a display curved surface.

In the example shown in FIG. 9, the CPU 11 superimposes and displays plural segmented regions for segmenting the vicinity area over the display image, and when one of the segmented regions is selected by the first operation, changes the inclination of the display curved surface so that the selected segmented region moves toward the back of the screen. When one of the segmented regions is selected by the second operation, the CPU 11 changes the inclination of the display curved surface so that the selected segmented region moves toward the front of the screen.

A display button 71 is a button for issuing a command to display the segmented regions 73a~73h. A non-display button 72 is a button for issuing a command not to display the segmented regions 73a~73h.

In FIG. 9, a mouse position (denoted by a solid black arrow) is indicated at the segmented region 73a. For example, when the segmented region 73a is selected by the first operation (for example, one click), the CPU 11 changes the inclination of the display curved surface so that the segmented curved surface 73a moves toward the back of the screen. Also for example, when the segmented region 73a is selected by the second operation (for example, double click), the CPU 11 changes the inclination of the display curved surface so that the segmented region 73a moves toward the front of the screen.

Figure 10:
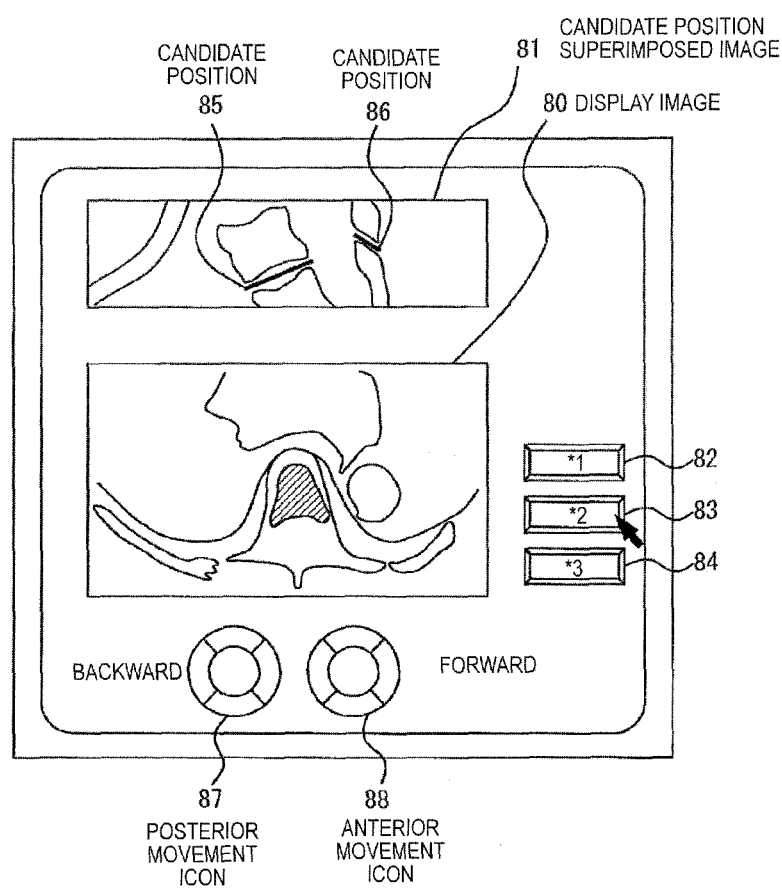
FIG. 10 is a screen example for selecting a display curved surface to be displayed from among plural candidates.

In FIG. 10, a candidate position superimposing image is presented for the user to select one region, when plural intervertebral disc regions are extracted from among the display images. In FIG. 10, the CPU 11 superimposes and displays a candidate position of the display curved surface over a conversion image, inputs information on the selected candidate position of the display curved surface, and creates a display image based on the display curved surface determined by the input information.

In an example shown in FIG. 10, candidate positions 85 and 86 are shown in a candidate position superimposing image 81 as objects to indicate the candidate positions of an intervertebral disc. The object indicating the position of the most appropriate intervertebral disc region is candidate position 85.

A next disc button 82 is a button for giving a command to change the intervertebral disc to be displayed (the shaded area shown in FIG. 10). When the next disc button 82 is pushed down, the CPU 11 searches, for example the next intervertebral disc along the Z-axis in the negative direction, and changes the candidate position superimposing image 81. Then in the case that only one intervertebral region is extracted, CPU 11 displays the display image 80 with the change of the candidate position superimposing image 81. On the other hand, in the case that plural intervertebral disc regions are extracted as shown in FIG. 10, the CPU 11 receives the specification of a candidate position 85 from the user without displaying the display image 80.

A correction button 83 of a curved surface is for enabling input of command information such as translation or change of inclination of a display curved surface. When the correction button 83 of a curved surface is pushed down, the CPU 11 sets a condition that a correction program can be executed. The correction program may also be set by an event-driven manner such as an input event by the user.

An ending button 84 is a button for ending the display of the display image 80.

A posterior movement icon 87 is a donut-shaped icon which is segmented into plural regions.

The posterior movement icon 87 corresponds to the regions in the display image 80, for changing the inclination of the display curved surface so that the selected segmented region moves toward the back (in a posterior direction) of the screen.

An anterior movement icon 88 is also a donut-shaped icon which is segmented into plural regions.

The anterior movement icon 88 corresponds to the regions in the display image 80, for changing the inclination of the display curved surface so that the selected segmented region moves toward the front (in an anterior direction) of the screen.

FIG. 10 shows the condition that the user selects a candidate position 85 using an input device and the CPU 11 creates and displays the display image 80 in accordance with the user's operation. Even if plural intervertebral disc regions are extracted by a screen interface shown in FIG. 10, through selection of a correct intervertebral disc region by the user, the display image 80 can be displayed including an intervertebral disc region.

Figure 11:
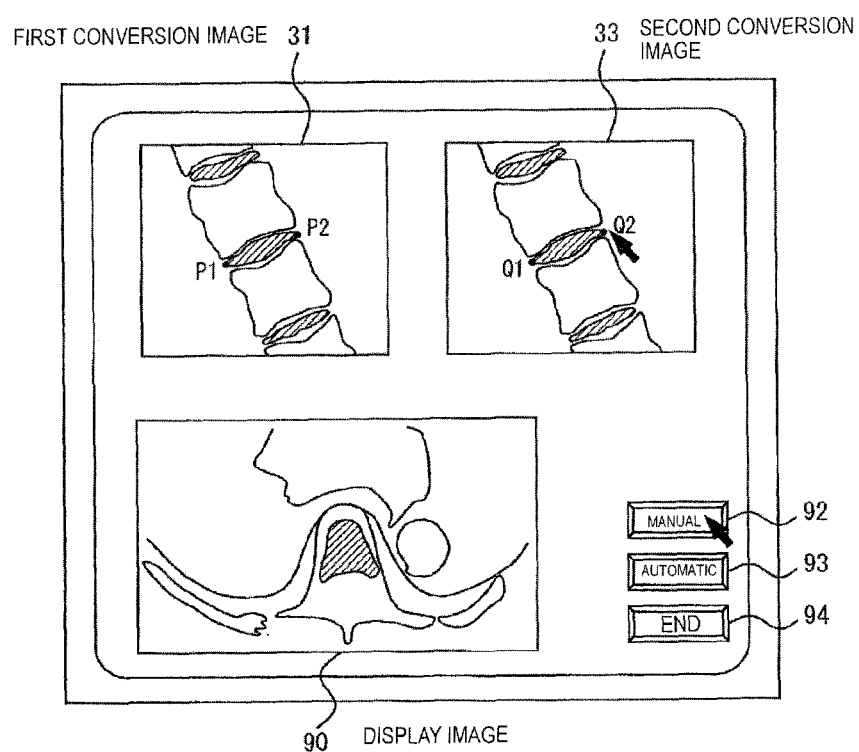
FIG. 11 is a screen example for manually selecting coordinate positions of feature points.

FIG. 11 shows a screen interface of a case in which a user selects coordinate positions of four feature points P1, P2, Q1 and Q2 via the input device.

In FIG. 11, a first conversion image 31, a second conversion image 33, a display image 90, a manual button 92, an automatic button 93 and an ending button 94 are displayed.

The manual button 92 is a button for the user to select coordinate positions of the four feature points.

The automatic button 93 is the button for switching the mode to the one in which the medical image processing device 1 specifies coordinate positions of the four feature points.

The ending button 94 is a button for ending image display.

As shown in FIG. 11, when the user selects four coordinate positions using an input device (the mouse 18, and the like), the CPU 11 specifies the selected four coordinate positions as four feature points P1, P2, Q1 and Q2, creates a display image 90 and displays the image on the display device 17.

Figure 12:
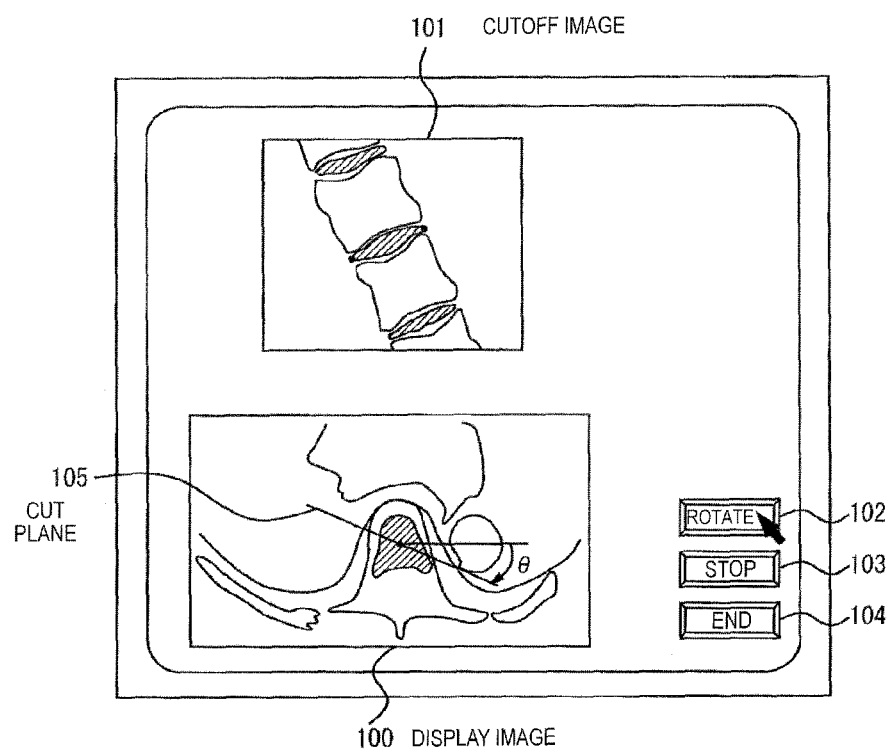
FIG. 12 is a screen example for consecutively displaying cutoff images.

FIG. 12 shows a screen example of a case in which a cutoff image is continually displayed with respect to a display image. In FIG. 12, the CPU continually executes a process of superimposing the position of a converted curved surface on a display image while rotationally transferring the position of the converted image, and displaying a cutoff image formed by the pixels that are extracted from plural cross-sectional images based on the position of the displayed converted image.

In FIG. 12, a display image 100, a cutoff image 101, a rotation button 102, a stop button 103 and an ending button 104 are displayed.

The rotation button 103 is a button for rotating a cut cross-section 105 which is superimposed and displayed on the display image 100.

The stop button 103 is a button for stopping the rotation of the cut cross-section 105.

The ending button 104 is a button for ending the display image.

As shown in FIG. 12, when the rotation button 102 is pushed down by a user, the CPU 11 rotates the cut cross-section 105 counterclockwise to change cut angle $\theta$ (angle formed between the cut cross-section and the horizontal axis), so as to create a cutoff image 101 in accordance with cut angle $\theta$ and display the image on the display device 17. Then CPU 11 repeats the rotation of the cut cross-section 105 as well as the creation and display of the cutoff image 101 in accordance with cut angle $\theta$ until the stop button 103 is pushed down. In addition, the cut cross-section 105 is not limited to a flat surface, and may also be a curved surface.

In this manner, the user can simultaneously perform radiographic image interpretation of the display image 100 in which the condition of an entire intervertebral disc can be visually identified and the cutoff image 101 in which the display image 100 is cut off at an arbitrary cut cross-section. Accordingly, FIG. 12 is an example of a screen interface suitable for radiographic image interpretation of an intervertebral disc.

Figure 13:
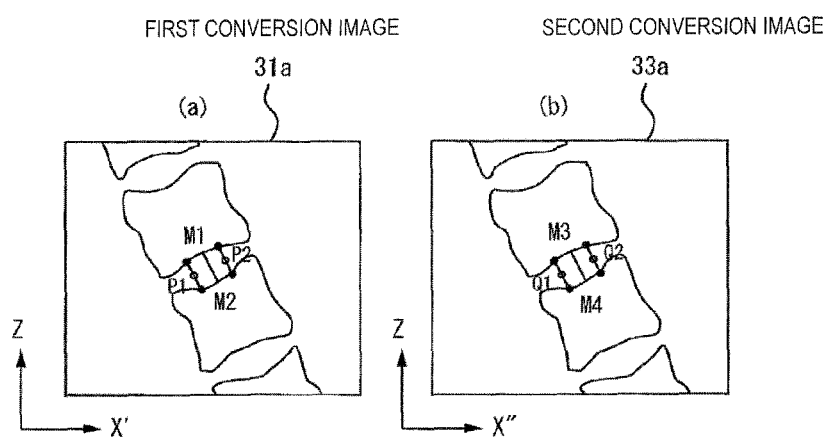
FIG. 13 is a view for explaining a second feature point specifying process.
Figure 14:
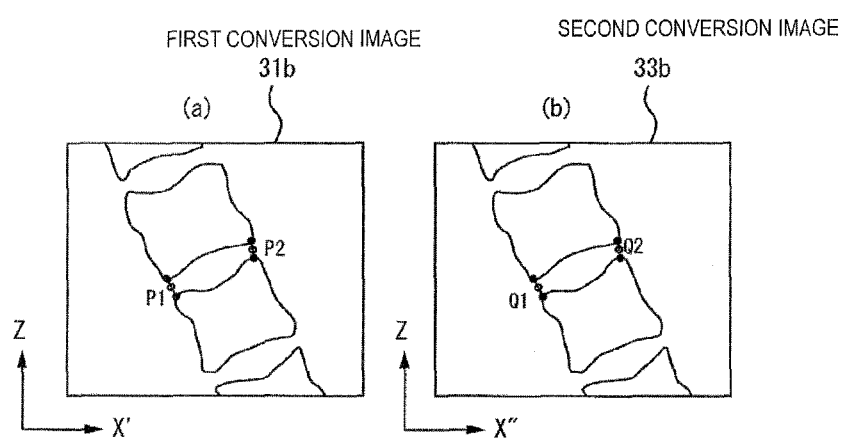
FIG. 14 is a view for explaining a third feature point specifying process.
Figure 15:
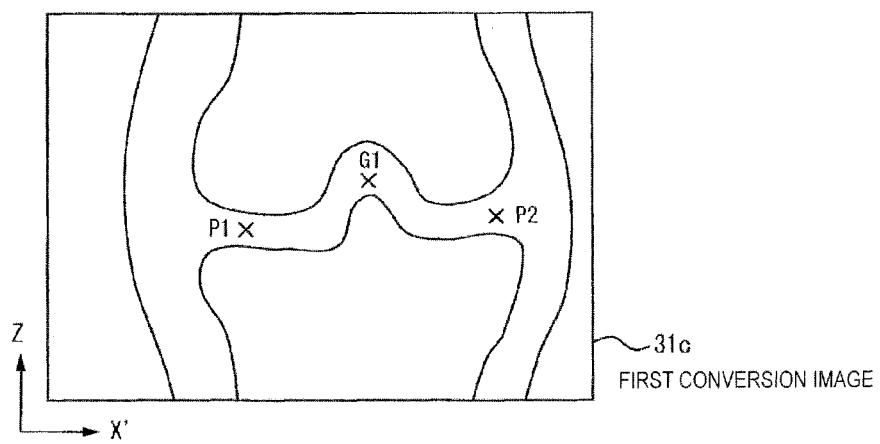
FIG. 15 is a view for explaining a fourth feature point specifying process.
Figure 15:
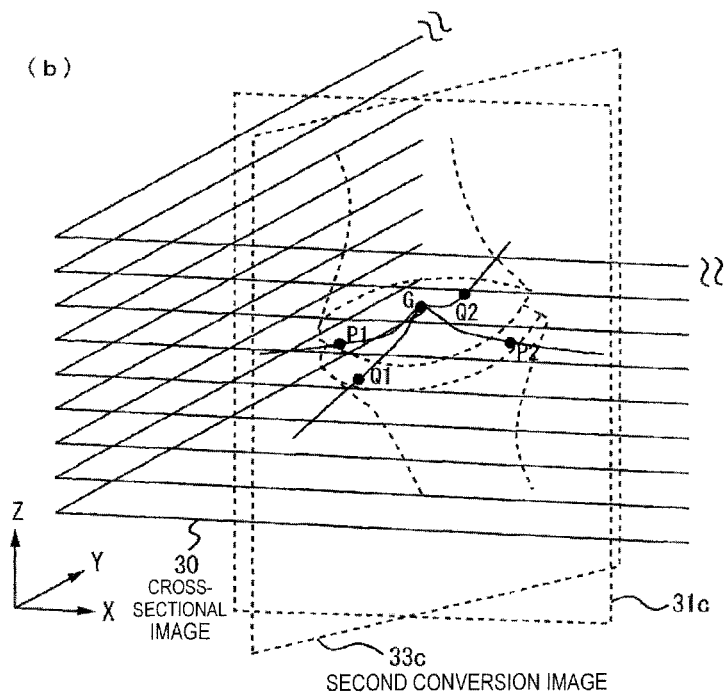

Next, a modification of the feature point specification process will be described referring to FIG. 13~FIG. 15. In FIG. 13~FIG. 15, the CPU 11 extracts bone tissue regions that are the region of bone tissue in a conversion image, and specifies feature points based on the distance between the facing bone tissue regions.

In FIG. 13 and FIG. 14, an intervertebral disc which is cartilage tissue exists between vertebrae is described as an example of interosseous tissue. Also, cartilage tissue which exists in a knee joint is described as an example of interosseous tissue in FIG. 15.

FIG. 13 shows a second feature-point specification process. The creation process of the first conversion image 31a and the second conversion image 33a is the same as the previous description.

The CPU 11 extracts two vertebral regions (bone tissue regions) with an intervertebral disc (cartilage tissue) therebetween on the basis of the first conversion image 31a. Next, the CPU 11 sets the coordinate positions having the maximum distance between the vertebral regions as M1 and M2, and extracts the line segment which passes through M1 and M2. M1 and M2 are the pixels that are included in the respective vertebral regions (bone tissue regions). Next, the CPU 11 extracts two line segments that are parallel to the line segment which passes through M1 and M2. The CPU 11 makes the parallel line segments, for example to be away from the line segment which passes through M1 and M2 by a predetermined distance. Both ends of the parallel line segments are the pixels included in the respective vertebral regions (bone tissue regions). Then the CPU 11 specifies the midpoint of the respective parallel line segments as feature points P1 and P2.

Also, the CPU 11 extracts two vertebral regions (bone tissue regions) with an intervertebral disc (cartilage tissue) therebetween on the basis of the second conversion image 33a. Next, the CPU 11 sets the coordinate positions having the maximum distance between the vertebrae as M3 and M4, and extracts the line segment which passes through M3 and M4. M3 and M4 are the pixels included in the respective vertebral regions (bone tissue regions). Then the CPU 11 extracts two line segments parallel with the line segment which passes through M3 and M4. The CPU 11 makes the parallel line segments, for example to be apart from the line segment which passes through M3 and M4 by a predetermined distance. Both edge points of the parallel line segments are the pixels included in the respective vertebral regions (bone tissue regions). Then the CPU 11 specifies the midpoint of the respective parallel line segments as feature points Q1 and Q2.

The processing after the specification of feature points is the same as the previous description. In addition, the number of conversion images is not limited to two, and three or more images can be used. Also, the number of feature points is not limited to four, and five or more (six or eight) feature points can be used.

In the second feature point specification process, vertebral regions (bone tissue regions) are extracted without extracting intervertebral disc regions (cartilage tissue regions), and feature points are specified on the basis of the vertebral regions (bone tissue regions). Since bone tissue can be extracted with high precision compared to other tissue in medical images such as CT images, feature points can also be specified with high precision.

FIG. 14 shows a third feature point specifying process. The process of creating the first conversion image 31b and the second conversion image 33b is the same as the previous description.

The CPU 11 extracts two vertebral regions (bone tissue regions) with an intervertebral disc (cartilage tissue) therebetween on the basis of the first conversion image 31b. Next, the CPU 11 extracts two line segments having the minimum distance between the vertebrae. Both edge points of the line segments are the pixels included in the respective vertebral regions (bone tissue regions). Then the CPU 11 specifies the midpoint of the respective line segments as feature points P1 and P2.

Also, the CPU 11 extracts two vertebral regions (bone tissue regions) with an intervertebral disc (cartilage tissue) therebetween on the basis of the second conversion image 33b. Next, the CPU 11 extracts two line segments having the minimum distance between vertebral regions. Both edge points of the line segments are the pixels included in the respective vertebral regions (bone tissue regions). Then the CPU 11 specifies the midpoint of the respective line segments as feature points Q1 and Q2.

The process after the specification of feature points the same as the previous description. In addition, the number of conversion images is not limited to two, and three or more images can be used. Also, the number of feature points is not limited to four, and five or more (six or eight) may be used.

In the third feature point specifying process, a vertebral region (bone tissue region) is extracted without extracting an intervertebral disc region (cartilage tissue region), and feature points are specified on the basis of the vertebral region (bone tissue region). Since bone tissue can be extracted with high precision compared to other tissue in medical images such as CT images, feature points can also be specified with high precision.

FIG. 15 shows the fourth feature point specifying process. The fourth feature point specifying process is suitable for applying to cartilage tissue which exists in a knee joint, and the like. The process of creating the first conversion image 31c and the second conversion image 33c is the same as previously described.

As shown in FIG. 15(a), the CPU 11 extracts two bone tissue regions with cartilage tissue therebetween on the basis of the first conversion image 31c, as in the second feature point specifying process or the third feature point specifying process. Then the CPU 11 specifies feature points P1 and P2 as in the second feature point specifying process or the third feature point specifying process.

Next, the CPU 11 calculates the midpoint of the P1 and P2 in the horizontal direction (X'-axis direction), and extracts the line segment which passes through the midpoint and extends in the longitudinal direction (Z-axis direction). Both edge points of the line segments are the pixels included in the respective bone tissue regions. Then the CPU 11 specifies the midpoint of the line segment as feature point G1.

Also as shown in FIG. 15(b), the CPU 11 extracts two bone tissue regions with cartilage tissue therebetween on the basis of the second conversion image 33c, as in the second feature point specifying process or the third feature point specifying process. Then the CPU 11 specifies feature points Q1 and Q2 as in the second feature pint specifying process or the third feature point specifying process.

Next the CPU 11 calculates the midpoint of the P1 and P2 in the horizontal direction, and extracts the line segments which passes through the midpoint and extends in the longitudinal direction. Both edge points of the line segment are the pixels included in the respective bone tissue regions.

Then CPU 11 specifies the midpoint of the line segment as feature point G2 (not shown in the diagram).

Next, the CU 11 specifies the average coordinate position of feature points G1 and G2 as feature point G.

The CPU then calculates the spline curve which passes through a sampling point on the line segment having the feature points as its edge points and has feature point G as its edge point. The spline curve is calculated so that it passes through the cartilage tissue region. For example, the CPU 11 may specify four or more feature points for each conversion image, so as to increase the coordinates for determining the spline curve.

Then the CPU 11 sets the assembly of the spline curves as a display curved surface. The process after the specification of the display curved surface is the same as previously described. The number of conversion images is not limited to two, and three or more images may be used.

In the fourth feature point specifying process, a bone tissue region is extracted without extracting a cartilage tissue region, and specifies feature points on the basis of the extracted bone tissue region. Since bone tissue can be extracted with high precision compared to other tissue in medical images such as CT images, feature points can also be specified with high precision.

Particularly, a display image created by the fourth feature point specifying process is the image in which the condition of an entire cartilage tissue can be visually identified even when the cartilage tissue is located between the bone tissues of complicated shapes such as a knee joint, thus is suitable for radiographic image interpretation of cartilage tissue.

As described above, the medical image processing device in Embodiment 1 repeats the process of creating a conversion image which includes interosseous tissue and plural bone tissue regions with interosseous tissue therebetween on the basis of plural cross-sectional images and specifying at least two points as feature points by a predetermined condition on the basis of the conversion image, as least two times using the conversion images having different conversion curved surfaces. Then the medical image processing device creates a display image by calculating a display curved surface showing the position of the pixels that constitute the display image on the basis of the feature points and extracting the pixel values corresponding to the pixels of the display curved surface from the plural cross-sectional images.

In MPR images, cut cross-sections usually have a flat surface. Therefore, three feature points need to be specified for determining a cut cross-section of an MPR image. However with three feature points, there are cases that the shape of a part of a cartilage tissue cannot be reflected to the feature points, thereby the condition of an entire cartilage tissue cannot be visually identified in a created image.

On the other hand, the medical image processing device in Embodiment 1 creates at least two conversion images, and specifies at least two feature points for each conversion image, that is, at least four feature points are specified. Therefore, the shape of cartilage tissue can be thoroughly reflected on the feature points, thereby making it possible to create a display image in which an entire cartilage tissue can be visually identified.

Embodiment 2

Next, Embodiment 2 will be described referring to FIG. 16~FIG. 24.

The medical image processing device 1 in Embodiment 2 creates and displays, in particular, a 3-dimensional image suitable for radiographic image interpretation of tissue such as an intervertebral disc.

First, a first display image creating process in Embodiment 2 will be described referring to FIG. 16~FIG. 19. In FIG. 16~FIG. 19, an intervertebral disc which is cartilage tissue that exists between vertebrae will be described as an example of interosseous tissue. Also, a CT image will be described as an example of a medical image.

Figure 16:
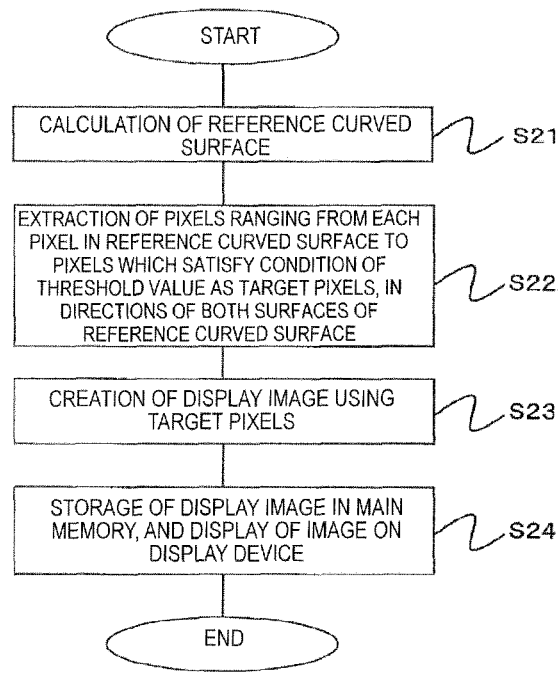
FIG. 16 is a flowchart showing the flow of a first display image creating process in Embodiment 2.

As shown in FIG. 16, the CPU 11 of the medical image processing device 1 calculates a reference curved surface (step S21). A reference curved surface is a curved surface to be the reference for creating a display image. It is preferable that a reference curved surface thoroughly passes through an entire cartilage tissue. Accordingly, the CPU 11 calculates the reference curved surface as in the display curved surface described in Embodiment 1.

Next, the CPU 11 extracts the pixels ranging from the respective pixels of the reference curved surface to the pixels which satisfy the condition of a threshold value as target pixels, in the direction of both surfaces of the reference curved surface (step S22).

Figure 17:
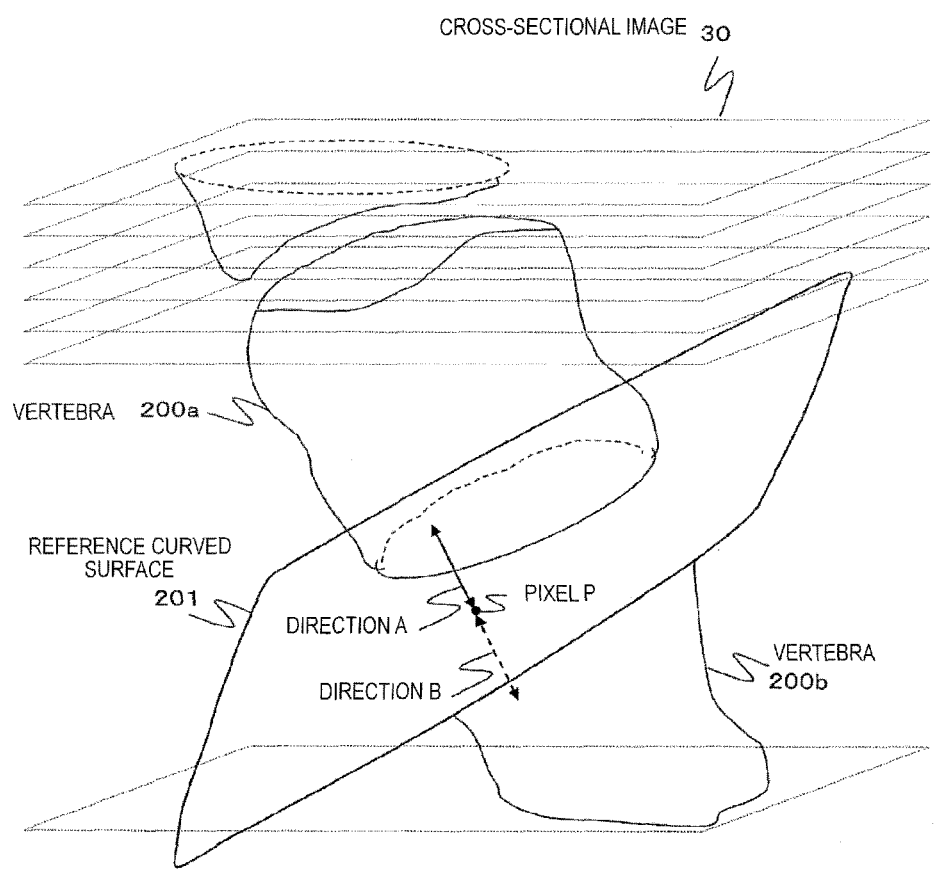
FIG. 17 is a view for explaining the first display image creating process.

As shown in FIG. 17, a reference curved surface 201 calculated in the same manner as the display curved surface in Embodiment 1 is a curved surface which passes through between a vertebra 200a and a vertebra 200b. The vertebra 200a is positioned in the upper part of the reference surface 201. The vertebra 200b is positioned in the lower part of the reference surface 201.

The "directions of both surfaces of the reference curved surface" in step S22 are the direction A and direction B shown in FIG. 17. Direction A is the direction ranging from the top surface of the reference curved surface 201 to the vertebra 200a which is positioned in the upper part of the reference curved surface 201. Direction B is the direction ranging from the undersurface of the reference curved surface 201 to the vertebra 200b which is positioned in the lower part of the reference curved surface 201.

The CPU 11 first specifies pixel P on the reference curved surface 201 which is the processing target. Next, the CPU 11 sets pixel P as a starting point, scans the pixels in direction A, and determines whether or not the pixel value of the respective pixels satisfies the condition of a threshold value. Here, the condition of a threshold value is defined based on the CT value of the bone tissue and cartilage tissue.

In an example of vertebrae and intervertebral discs shown in FIG. 17, the condition of the threshold value can be set, for example to be greater than the CT value of the surrounding tissue of the vertebrae and intervertebral discs (ligament or muscle) and smaller than the CT value of the vertebra, by setting the upper limit and the lower limit. In other words, the CPU 11 scans the pixels from pixel P toward direction A for extracting the pixels of the intervertebral disc. Then when the scanned pixel reaches the one having the CT value of the vertebra or the surrounding tissue, the CPU 11 determines that the scanning of the intervertebral disc region is completed, and ends the extraction of target pixels. In the same manner, the CPU 11 scans the pixels from pixel P toward direction B for extracting the pixels of the intervertebral disc. Then when the scanned pixel reaches the one having the CT value of the vertebra or the surrounding tissue, the CPU 11 determines that the scanning of the intervertebral disc area is completed, and ends the extraction of the target pixels.

Also, the condition of the threshold value may be set, for example, as being smaller than the CT value of a vertebra with only the upper value. In this case, the pixels of an extraction target may be limited to be within the space including an entire intervertebral disc (hereinafter referred to as "extraction target space"). For example, an extraction target space may be set as the inside of a cylinder which extends in the direction orthogonal to the reference curved surface 201. The radius of the cylinder is calculated, for example by multiplying the distance between coordinates P1 and P2 in FIG. 3 of Embodiment 1 by the excess coefficient. Then the CPU 11 extracts the pixels of the intervertebral disc by scanning the pixels from pixel P toward direction A. When the scanned pixel reaches the one having the CT value of the vertebra or the one in the outside of the extraction target space, the CPU 11 determines that the scanning of the intervertebral disc region is completed, and ends the extraction of the target pixels. In the same manner, the CPU 11 extracts the pixels of the intervertebral disc by scanning the pixels from pixel P toward direction B. When the scanned pixel reaches the one having the CT value of the vertebra or the one in the outside of the extraction target space, the CPU 11 determines that the scanning of the intervertebral disc region is completed, and ends the extraction of the target pixels.

Here, the method of determining direction A and direction B will be described. In a first determination method, the CPU 11 determines direction A and direction B for each pixel on the reference curved surface 201. For example, the CPU 11 calculates a normal vector in each pixel, and the positive direction and the negative direction of the normal vector is set as direction A and direction B for each pixel on the reference curved surface.

Also in a second determination method, the CPU 11 determines single direction A and single direction B with respect to all pixels on the reference curved surface 201. For example, the CPU 11 calculates a normal vector in the representative point (for example, the barycenter of the feature points shown in FIG. 5) of the reference curved surface 201, and sets the positive direction and the negative direction of the normal vector in the representative point as direction A and direction B. Also for example, the CPU 11 sets the upward direction and the downward direction of the direction orthogonal to the slice plane of the cross-sectional image 30 as direction A and direction B.

The CPU 11 may store the density of the target pixels in the main memory 12 as it is, or may binarize the density based on the CT value of the intervertebral disc, etc. and store the binarized density in the main memory 12. In other words, the CPU 11 may store and keep only the density data of target pixels in the main memory 12 from the density data of the respective cross-sectional images 30. Also, the CPU 11 may store the pixels as binarized data in the main memory 12, for example by setting target pixels as "1" and non-target pixels as "0".

Also, as shown in FIG. 18, the CPU 11 may store data in the main memory 12 independently of the cross-sectional images 30 in place of storing data for each cross-sectional image 30, in order to save memory capacity of the main memory 12.

The data structure of a storage area 211 shown in FIG. 18(a) stores x-coordinate of a target pixel, y-coordinate of the target pixel, the distance from the reference curved surface to the target pixel, and the density of the target pixel. For example, the first data has the x-coordinate of "x(1)", y-coordinate of "y(1)", distance of "r(1) and density of "I(1)". With the storage area 211, the CPU 11 is capable of creating a 3-dimensional display image using both the surface modeling method and the volume rendering method.

A storage area 212 shown in FIG. 18(b) has the data structure that stores only the distance from the reference curved surface 201 to a target pixel. With the storage region 212, the CPU 11 is capable of creating an approximative depth image. Each section of data in any of the storage area 211 and the storage area 212 is stored corresponding to the pixels in the reference curved surface 201.

The explanation returns to FIG. 16. The CPU 11 creates a display image using target pixels (S23). The CPU 11 may create a display image using the previously mentioned method such as the surface modeling method or volume rendering method, or may create a display image as an approximative depth image. Also, CPU 11 may create a display image by combining these methods.

Figure 19:
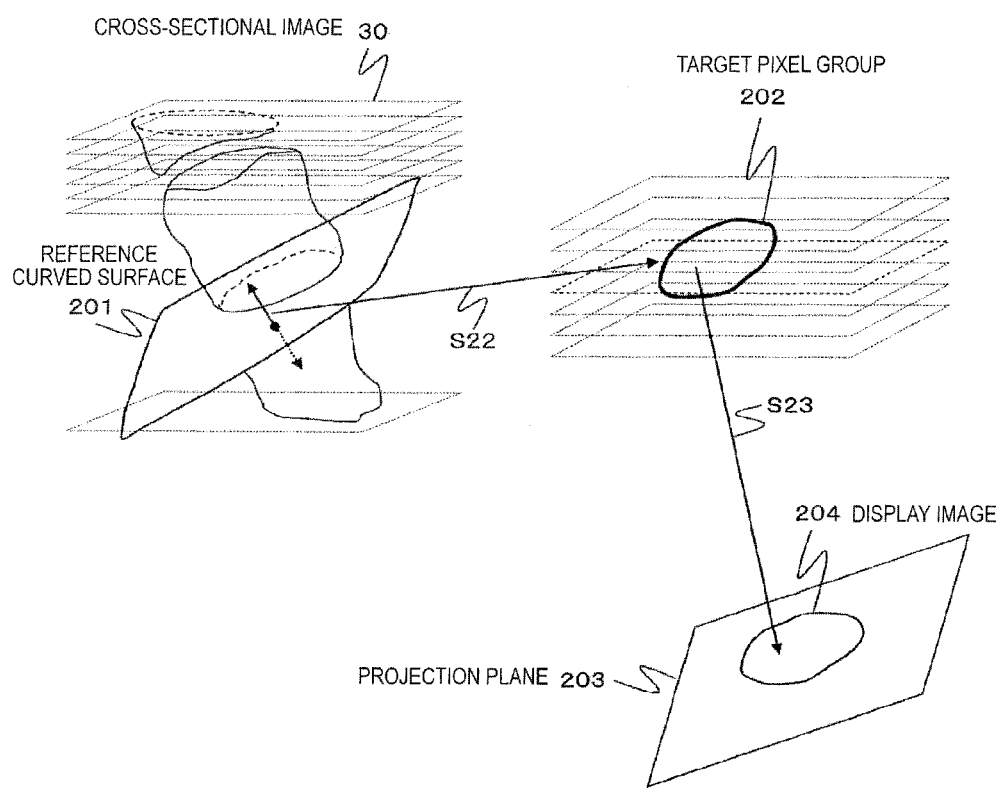
FIG. 19 is a view for explaining the first display image creating process.

As shown in FIG. 19, the CPU 11 extracts a target pixel group 202 in step S22. Then in step S22, the CPU 11 records the pixel values that constitute a display image 204 on a projection plane 203 by any of the previously mentioned method using the target pixel group 202. Here, recording in the projection plane 203 means to store the pixel values in a storage area which is reserved as the projection plane 203.

The explanation returns to FIG. 16. The CPU 11 stores the display image 204 in the main memory 12 as well as in the display memory 15, and displays the display image 204 on the display device 17 (S24).

The display image 204 created by the above-described procedure is a 3-dimensional image in which the condition of an entire intervertebral disc can be visibly identified, which is suitable for radiographic image interpretation of an intervertebral disc. In particular, the CPU 11 extracts the pixels of an intervertebral disc which exists on both surfaces of the reference curved surface 201 as target pixels in the first display image creating process, which makes it possible to apply various 3-dimensional image creation methods.

Figure 20:
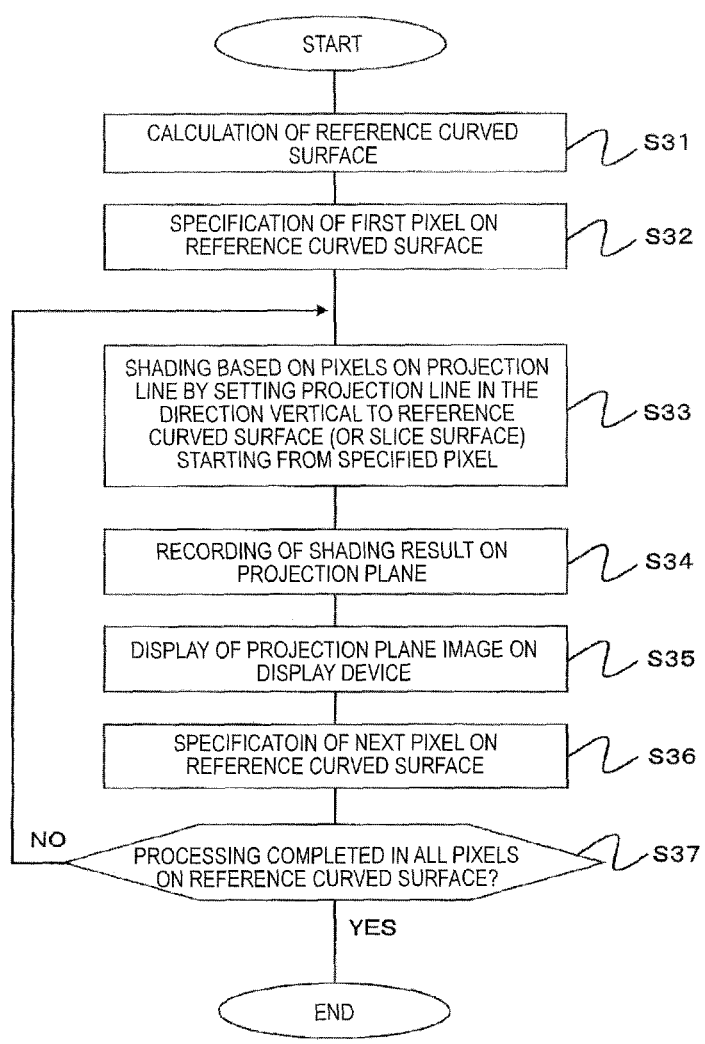
FIG. 20 is a flowchart showing the flow of a second display image creating process in Embodiment 2.
Figure 21:
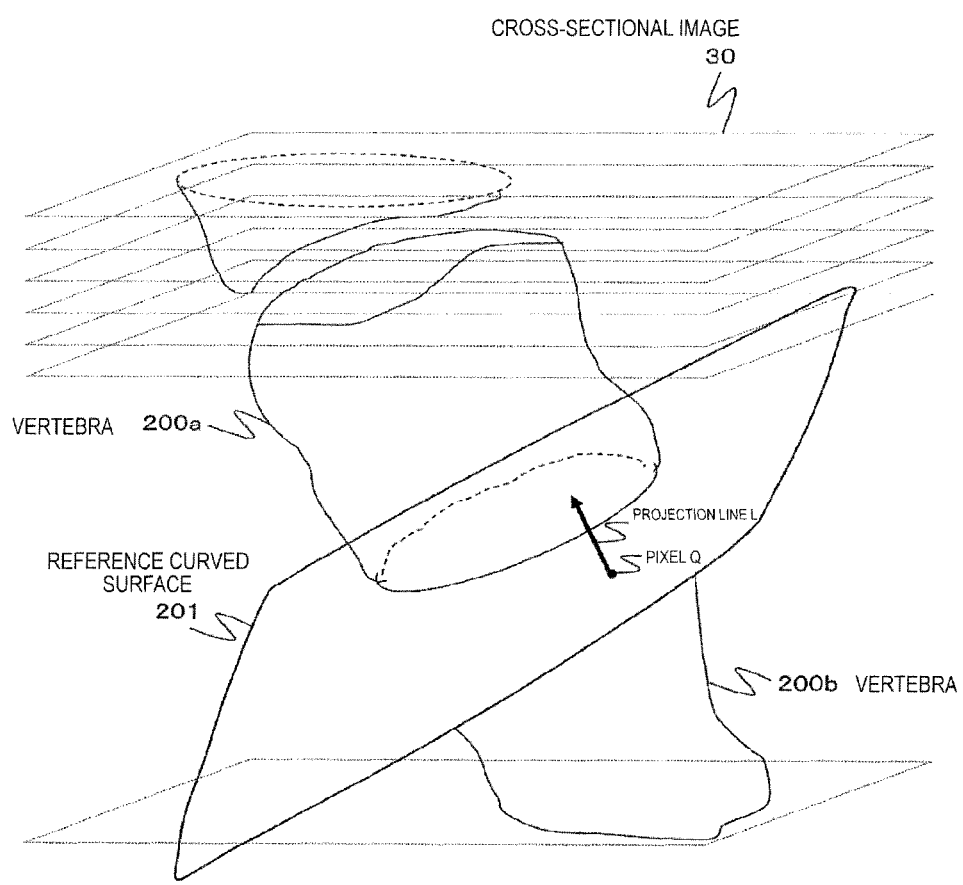
FIG. 21 is a view for explaining the second display image creating process.
Figure 22:
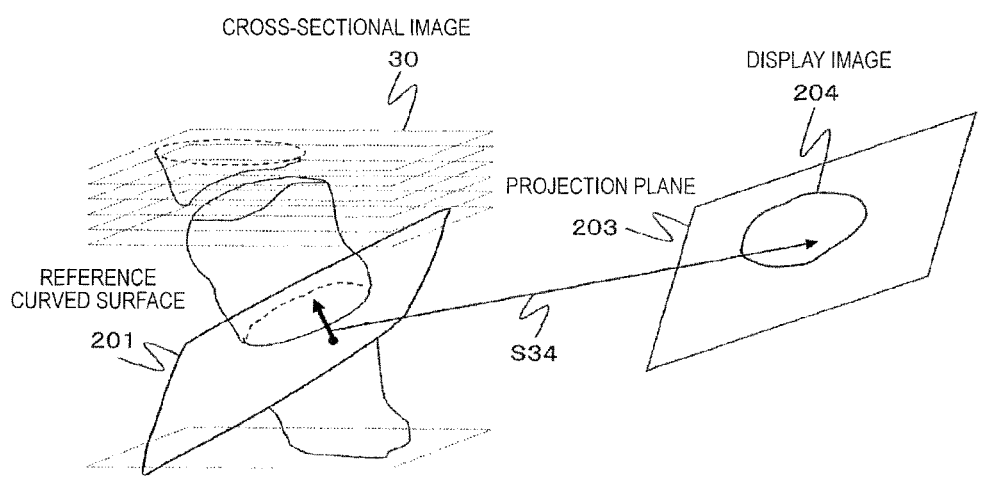
FIG. 22 is a view for explaining the second display image creating process.

Next, the second display image creation process in Embodiment 2 will be described referring to FIG. 20~FIG. 22. In FIG. 20~FIG. 22, an intervertebral disc exists between vertebrae will be described as an example of interosseous tissue. Also, a CT image is described as an example of a medical image. The second display image creation process is preferable for creating a display image 204 using the volume rendering method.

As shown in FIG. 20, the CPU 11 of the medical image processing device 1 calculates the reference curved surface 201 (step S31). The CPU 11 calculates the reference curved surface 201 in the same manner as in the display curved surface of Embodiment 1.

Next, the CPU 11 specifies the first pixel on the reference curved surface 201 (step S32). The CPU 11 specifies all pixels on the reference curved surface 201 by combining step S32 and step S36 to be described below, and repeats the processing in step S33~step S35 to be described below.

Next, CPU 11 defines a projection line in the direction vertical to the reference curved surface 201 having a specified pixel as its starting point, and performs shading on the basis of the pixels on the projection line (step S33). The shading is the process of calculating luminance of a surface at the time of observing a tissue surface from the starting point.

Also when a comprehensive inclination of the reference curved surface 201 is close to a slice plane of the cross-sectional image 30, the CPU 11 may define a projection line in the direction vertical to the slice plane having a specified pixel as its starting point and perform shading based on the pixels on the projection line.

For example, in a case that a projection surface 203 in the upper part of the reference curved surface 201 is set, as shown in FIG. 21, the CPU 11 sets projection line L in the direction of the vertebra 200a which is positioned in the upper part from the reference curved surface 201 with pixel Q (=the pixel specified in step S32 and step S36) on the reference curved surface 201 as its starting point, and performs shading using the pixels of projection line L and the pixels in the vicinity thereof.

The explanation returns to FIG. 20. The CPU 11 records the result of shading in the projection plane 203 (step S34). Then the CPU 11 stores the image of the projection plane 203 in the display memory 15, and displays the image of the projection plane 203 on the display device 17 (step S35). The processing of step S35 may be performed, for example by each scan line in the display of the display device 17 in place of performing by each pixel.

As shown in FIG. 22, the CPU 11 records the result of shading in the projection plane 203 in step S34. In the second display image creation process, the CPU 11 directly calculates the pixel values that constitute the display image 204, without extracting the pixels that are equivalent to an intervertebral disc. Accordingly, the display velocity of the display image 204 increases.

The explanation returns to FIG. 20. The CPU 11 specifies the next pixel on the reference curved surface 201 (step S36). Next, the CPU 11 determines whether or not the processing of all pixels on the reference curved surface 201 is completed (step S37). When the processing of all pixels is not completed (NO in step S37), the CPU 11 repeats the processing from step S33. When the processing of all pixels is completed (YES in step S37), the CPU 11 ends the processing. When the processing is ended, the entire display image 204 is displayed on the display device 17.

The display image 204 created by the above-described procedure is an image in which the condition of an entire intervertebral disc can be 3-dimensionally visualized, which is preferable for radiographic image interpretation of an intervertebral disc. Especially in the second display image creation processing, the CPU directly calculates the pixel values that constitute the display image 204 without extracting the pixels of an intervertebral disc, which makes it possible to increase the display velocity of the display image 204.

In the previously described first display image creation processing and the second display image creation processing, the CPU 11 of the medical image processing device 1 calculates the reference curved surface 201 in the same manner as it calculates the display curved surface in Embodiment 1, so as to create the display image 204 based on the pixels between one surface or both surfaces of the reference curved surface 201 and the bone tissue. Such created display image 204 is an image in which the condition of an entire intervertebral disc can be 3-dimensionally visualized, which is preferable for radiographic image interpretation of an intervertebral disc.

Figure 23:
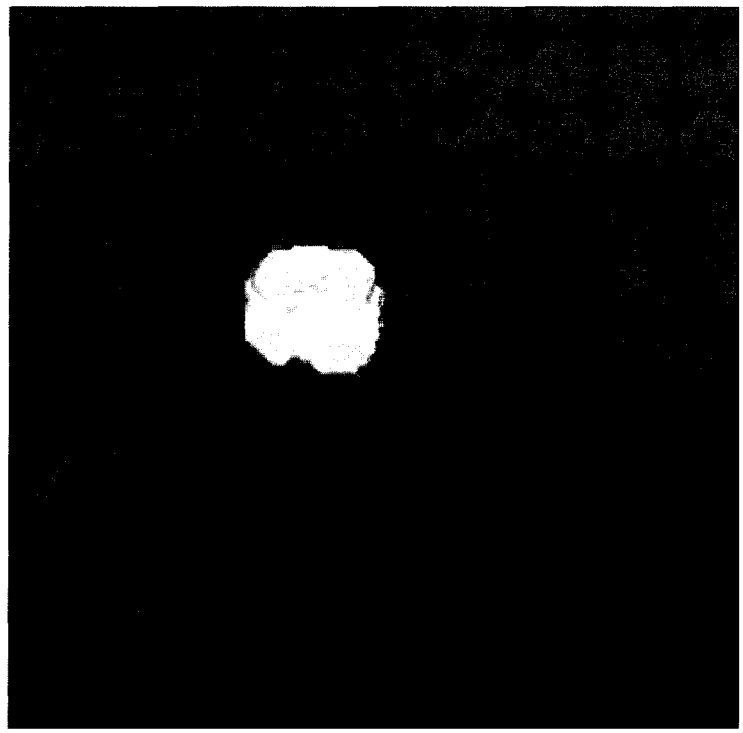
FIG. 23 is an example of a display image of a normal intervertebral disc.
Figure 24:
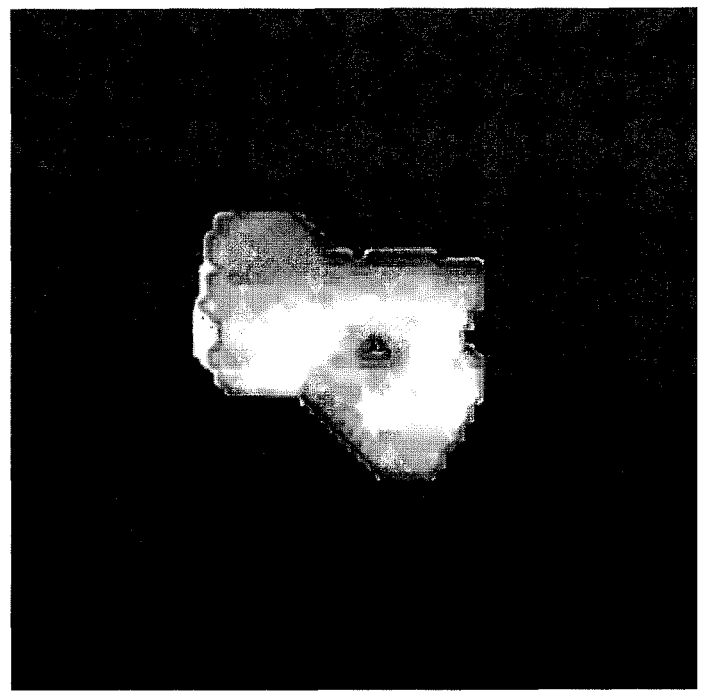
FIG. 24 is an example of a display image of an abnormal intervertebral disc.

Next, an example of display image creation in Embodiment 2 will be described referring to FIG. 23 and FIG. 24. In FIG. 23 and FIG. 24, an intervertebral disc which is cartilage tissue exists between vertebrae is described as an example of interosseous tissue. Also, a CT image is described as an example of a medical image.

FIG. 23 is a display image which is created as a 3-dimensional image of a normal intervertebral disc by the medical image processing device 1 of Embodiment 2 using the surface modeling method. The CPU 11 of the medical image processing device 1 extracted the pixels which belong to one intervertebral disc between two vertebrae as target pixels in accordance with the flowchart shown in FIG. 16, and created a display image by applying the surface modeling method. The display image shown in FIG. 23 is the image in which the original one is enlarged three times. By applying the surface modeling method, the places having a sharp inclination are displayed in gray or black.

FIG. 24 is a display image created by the medical image processing device 1 in Embodiment 2 as a 3-dimensional image showing an abnormal intevertebral disc by combining the surface modeling method and the approximative depth image creation method. The CPU 11 of the medical image processing device 1, in accordance with the flowchart shown in FIG. 16, extracted the pixels that belong to one intervertebral disc exists between two vertebrae as target pixels, and created a display image by combining and applying the surface modeling method and the approximative depth image creation method. The display image shown in FIG. 24 is the mage in which the on one is enlarged seven times. By applying the surface modeling method, the places having a sharp inclination are displayed in gray or black. Also by applying the approximative depth image creation method, the places in an intervertebral disc having a dent or hole are displayed in gray or black. This is because the pixels are displayed in white when the distance ranging from the reference curved surface to the target pixels is great, and are displayed in colors ranging from gray to black as the distance gets smaller.

As shown in FIG. 23, if an intervertebral disc is normal, the overall image is displayed in white color without having gray or black pixels inside. On the other hand, as shown in FIG. 24, if the image is of an abnormal intervertebral disc with dents or holes, the places with dents or holes are displayed in gray or black. In this manner, with a display image created by the medical image processing device in Embodiment 2, it is possible to easily identify whether a target intervertebral disc is a normal disc or an abnormal disc with dents or holes. In other words, a display image created by the medical image processing device 1 of Embodiment 2 is an image in which the condition of an entire tissue, even when the tissue is of a small one such as an intervertebral disc, can be 3-dimensionally visualized, which is preferable for radiographic image interpretation of an intervertebral disc.

Embodiment 3

Next, Embodiment 3 will be described referring to FIG. 25~FIG. 27. Non-patent Document 1 merely evaluates deformation of a vertebral body caused by osteoporosis quantitatively, and a technique of constructing a 3-dimensional image of a vertebral body separated one by one with high precision is not taken into consideration. Also including other known techniques, the technique of constructing a 3-dimensional image of a vertebral body separated one by one with high precision has not yet been disclosed. A vertebral body means the columnar part of a vertebra. The spine consists of plural connected vertebrae which is formed by, from the head side, seven cervical vertebrae, twelve thoracic vertebrae and five lumbar vertebrae, and there are sacral vertebrae and the coccyx underneath thereof. When viewed from the side of a human body, the cervical vertebrae, thoracic vertebrae, lumbar vertebrae and sacral vertebrae are curved back and forth respectively. The degree of curvature varies with each individual, and it has been difficult to separate vertebral bodies one by one with high precision using the conventional techniques. On the other hand, if vertebral bodies can be separated one by one with high precision, it will be useful for facilitating measurements to meet various diagnostic objectives. The medical image processing device 1 in Embodiment 3, in particular, separates vertebral bodies one by one and constructs a 3-dimensional image (=display image) of a single vertebral body.

First, the display image creation process in Embodiment 3 will be described referring to FIG. 25 and FIG. 26. In FIG. 25 and FIG. 26, a CT image is described as an example of a medical image.

Figure 25:
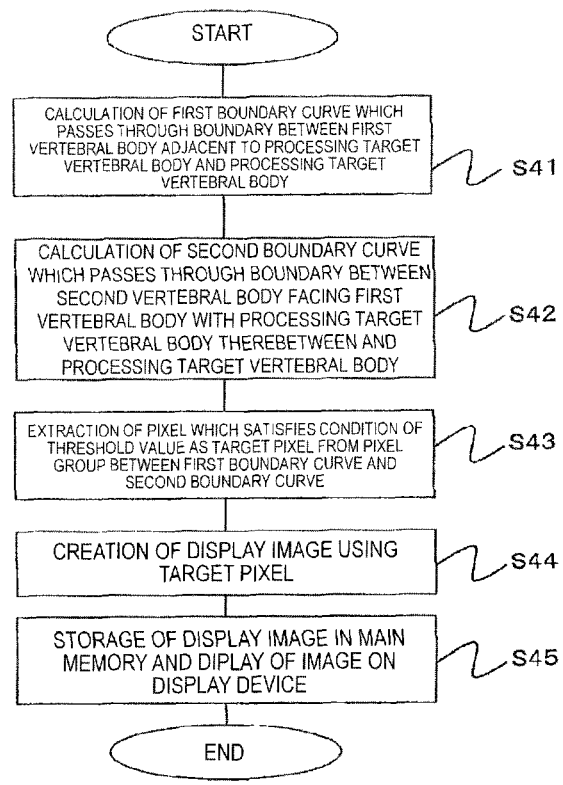
FIG. 25 is a flowchart showing the flow of a display image creating process in Embodiment 3.

FIG. 25 is a flowchart of a case that a target vertebral body exists between two adjacent vertebral bodies. However, the present invention is not limited to this example, and is applicable to a vertebral body which exists among one vertebral body and other tissues such as thoracic vertebrae in the top section or lumbar vertebrae in the lowest section.

As shown in FIG. 25, the CPU 11 of the medical image processing device 1 calculates a first border curved surface which passes through the border between a first vertebral body adjacent to a target vertebral body and the target vertebral body (step S41). A first border curved surface 301 shown in FIG. 26 passes through a vertebral body positioned in the lower section of the target vertebral body and the target vertebral body.

The border curved surface is a curved surface to be the border at the time of extracting the pixel group to be the basis of a display image. It is preferable that a border curved surface separates the border between the adjacent vertebral bodies with high precision. Therefore, the CPU 11 calculates the first border curved surface in a similar manner as calculating a display curved surface in Embodiment 1. In this regard, however the CPU 11 creates, as a conversion image, an image of the spine which is cut longitudinally, including a part of a target vertebral body and a part of plural intervertebral discs that are adjacent to the target vertebral body. Since the display curved surface in Embodiment 1 thoroughly passes through an entire intervertebral which is the border between adjacent vertebral bodies, the first border curved surface to be calculated in the same manner as the display curved surface in Embodiment 1 may be the curved surface capable of separating the border of adjacent vertebral bodies with high precision.

Next, the CPU 11 calculates a second border curved surface which passes through the border between a second vertebral body facing the first vertebral body having the target vertebral body therebetween and the target vertebral body (step S42). As for the conversion image, the same one as in step S41 or a different one may be used. A second border curved surface 302 shown in FIG. 26 passes through the border between the vertebral body positioned in the upper section from the target vertebral body and the target vertebral body. It may also be that the first border curved surface 301 which passes through the border between the vertebral body positioned in the upper section from the target vertebral body and the target vertebral body and the second border curved surface 302 which passes through the border between the vertebral body positioned in the lower section from the target vertebral body and the target vertebral body.

Next, the CPU 11 extracts the pixels which satisfy the condition of a threshold value as target pixels from among the pixel group between the first border curved surface 301 and the second border curved surface 302 (step S43). In concrete terms, the CPU 11 extracts the pixels which satisfy the condition of a threshold value as target pixels by scanning the pixels ranging from the pixels on the first border curved surface 301 toward the direction of the second border curved surface 302. The extracted target pixels are equivalent to the pixels of the processing target vertebral body. Then the CPU 11 completes the extraction of the target pixels when the extraction reaches the pixels on the second border curved surface 302. The direction for scanning the pixels may be determined in the same manner as the method of determining direction A and direction B in Embodiment 2.

The condition of a threshold value may be set, for example to be greater than the CT value of the vicinity tissue of a vertebral body and smaller than the value in which the CT value of the vertebral body is multiplied by the excess coefficient, by setting the upper limit and the lower limit. Also, the condition of a threshold value may be set as the value which is smaller than the value in which the CT value of the vertebral body is multiplied by the excess coefficient, by setting only the upper limit. It may also be set, for example by limiting the pixels to be an extraction target within an extraction target space (as in Embodiment 2).

Also, the CPU 11 may store the density of target pixels as it is in the main memory 12 as in Embodiment 2, or may binarize the density and store them in the main memory 12. Also, the CPU 11 may fill special values (for example, the value of −1001 and less) in the pixels outside of the first border curved surface and the second border curved surface when viewed from the processing target vertebral body.

Also as shown in FIG. 18 in Embodiment 2, for saving memory capacity of the main memory 12, the CPU 11 may store data in the main memory 12 independently of the cross-sectional images 30 in place of storing data for each cross-sectional image 30.

Next, the CPU 11 creates a display image using the target pixels (step S44). The CPU 11, as in Embodiment 2, may create a display image using the method such as the surface modeling method or volume rendering method, or may create a display image as an approximative depth image. Also, CPU 11 may create a display image by combining these methods.

Figure 26:
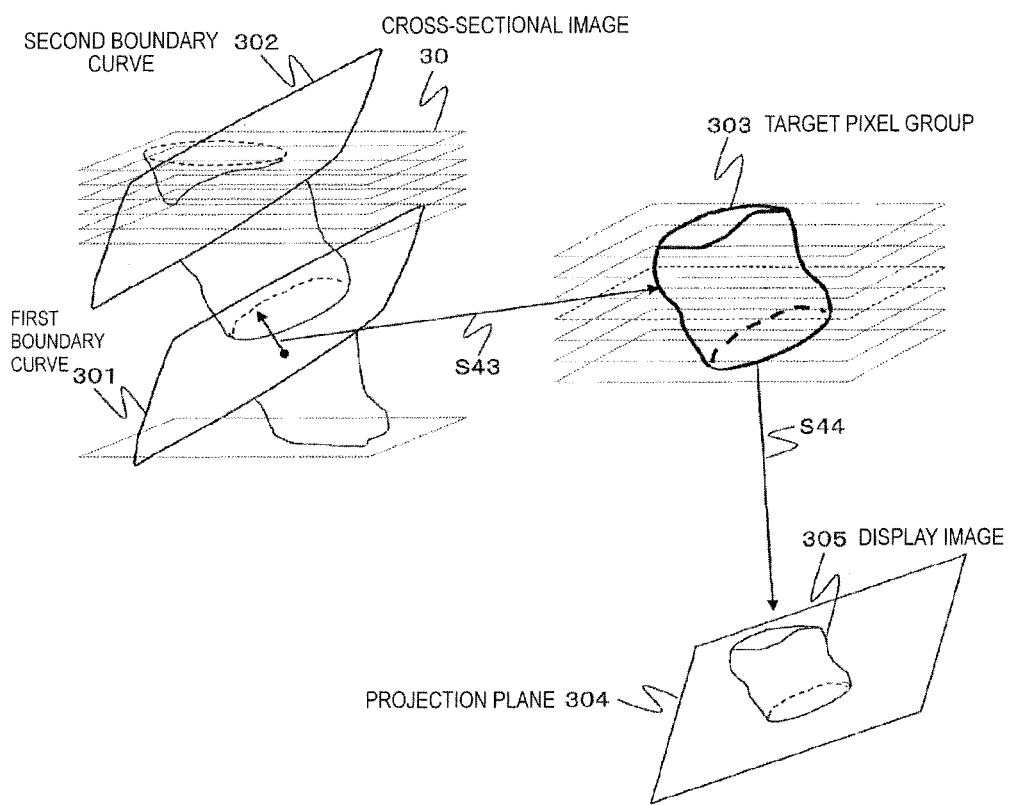
FIG. 26 is a view for explaining the display image creating process in Embodiment 3.
Figure 27:
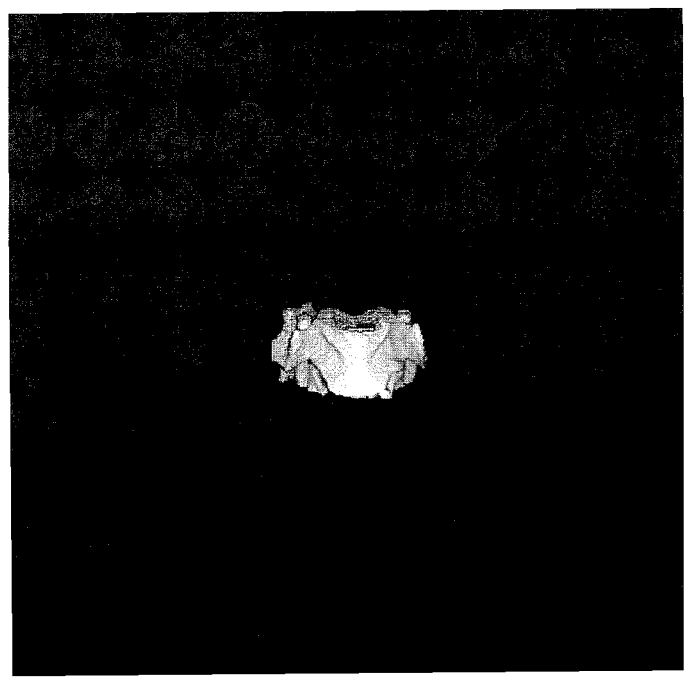
FIG. 27 is an example of a 3-dimensional image of an individual intervertebral body.

As shown in FIG. 26, the CPU 11 extracts a target pixel group 303 in step S43. Then the CPU 11, in step S44, records the pixel values that constitute a display image 305 in a projection plane 304 using the target pixel group 303 by any of the previously mentioned methods. Here, recording in the projection plane 304 means to store the pixel values in a storage area which is reserved as the projection plane 304.

Next, the CPU 11 stores the display image 305 in the main memory 12 as well as in the display memory 15, and displays the display image 305 on the display device 17 (step S45).

The display image 305 created by the above-described procedure is a 3-dimensional image constructed by separating single vertebral bodies one by one, which is suitable for making various diagnosis. Especially in the display image creation process in Embodiment 3, the CPU 11 extracts the pixels which satisfy the condition of a threshold value (=pixels of the target vertebral body) as target pixels from among the pixel group between the first border curved surface 301 and the second border curved surface 302, thereby facilitating measurements to meet various diagnostic objectives (for example, the volume of a vertebral body, the length in a predetermined direction of a vertebral body, and the area of a convex portion in a vertebral body).

Next, an example of display image creation in Embodiment 3 will be described referring to FIG. 27. The 3-dimensional image shown in FIG. 27 is constructed by separating a single vertebral body one by one. The pixel group to be the basis for the 3-dimensional image shown in FIG. 27 is extracted as target pixels, which enables the display thereof by changing the viewpoint. Therefore, it is possible to make an accurate diagnosis without missing an abnormal portion. Also, it is useful for facilitating measurements to meet various objectives of diagnosis.

The preferable embodiments of the medical image processing device according to the present invention have been described referring to the attached drawings. However, the present invention is not limited to these embodiments. It is obvious that persons skilled in the art can make various kinds of alterations or modifications within the scope of the technical idea disclosed in this application, and it is understandable that they belong to the technical scope of the present invention.

DESCRIPTION OF REFERENCE NUMERALS

1: medical image processing device, 30: cross-sectional image, 31, 31a, 31b and 31c: first conversion image, 32: first intervertebral disc region, 33, 33a, 33b and 33c: second conversion image, 40, 41 and 42: straight line, 43: half line, 50, 60, 70, 80, 90 and 100: display image, 51: central area, 52: vicinity area, 73a~73h: segmented region, 81: candidate position superimposing image, 85 and 86: candidate position, 87: posterior movement icon, 88: anterior movement icon, 101: cutoff image, 105: cut plane, 201: reference curved surface, 204: display image, 301: first border curved surface, 302: second border curved surface, 305: display image

The invention claimed is:

1. A medical image processing device which creates a display image formed by the pixels of plural cross-sectional images, to be displayed on a display device for radiographic image interpretation of interosseous tissue or bone tissue, comprising:
  a conversion image creation unit configured to create a conversion image including the interosseous tissue and plural bone tissues having the interosseous tissue therebetween, on the basis of the plural cross-sectional images;
  a feature point specification unit configured to execute a process, for each conversion image, of specifying at least two points as feature points by a predetermined specifying condition using at least two conversion images having different conversion curved surfaces showing the position of the pixels that constitute the conversion image;
  a display image creation unit configured to calculate a reference curved surface for creating the display image on the basis of the feature points and to create the display image on the basis of the reference curved surface; and
  a display unit configured to display the display image on the display device.

2. The medical image processing device according to claim 1, wherein the display image creation unit sets a display curved surface showing the position of the pixels that constitute the display image as the reference curved surface, and creates the display image by extracting the pixel values corresponding to the pixels of the display curved surface from the plural cross-sectional images.

3. The medical image processing device according to claim 2, wherein:
  the display image creation unit inputs information on a command for translating the display curved surface or for changing an inclination of the display curved surface, and recreates the display image in accordance with the input information; and
  the display unit, when the display image is recreated by the display image creation unit, updates and displays the display image.

4. The medical image processing device according to claim 3, wherein the display image creation unit:
  transfers the display curved surface to the back of the screen when the central area of the interosseous tissue region in the display image displayed on the display device is selected by a first operation;
  transfers the display curved surface to the front of the screen when the central area is selected by a second operation which is different from the first operation;
  changes the inclination of the display curved surface, when the vicinity area of the interosseous tissue region in the display image displayed on the display device is selected by the first operation, so that the selected vicinity area moves to the back of the screen; and
  changes the inclination of the display curved surface, when the vicinity area is selected by the second operation, so that the selected vicinity area moves to the front of the screen.

5. The medical image processing device according to claim 4, wherein:
  the display unit superimposes and displays plural segmented regions in which the vicinity area is segmented on the display image; and
  the display image creation unit changes the inclination of the display curved surface, when one of the segmented regions is selected by the first operation, so that the selected segmented region moves to the back of the screen, and changes the inclination of the display curved surface, when one of the segmented regions is selected by the second operation, so that the vicinity of the selected segmented region moves to the front of the screen.

6. The medical image processing device according to claim 2, wherein the display unit superimposes and displays the position of the conversion curved surface on the display image while rotationally transferring the position of the conversion curved surface, and continually executes the processing of displaying a cutoff image formed by the pixels extracted from the plural cross-sectional images based on the position of the displayed conversion curved surface.

7. The medical image processing device according to claim 2, wherein the feature point specifying unit extracts an interosseous tissue region which is a region of interosseous tissue in the conversion image, and specifies two points that are farthest away from each other in the interosseous tissue region as feature points.

8. The medical image processing device according to claim 2, wherein the feature point specifying unit extracts a bone tissue region which is a region of the bone tissue in the conversion image, and specifies the feature points based on the distance between the facing tissue regions.

9. The medical image processing device according to claim 2, wherein the conversion image creation unit sets the straight line including the most pixels of the bone tissue from among straight lines extending in one axis direction of the interosseous tissue region in the cross-sectional image as the center line, and calculates the curved surface including the straight line parallel to the center line as the conversion curved surface.

10. The medical image processing device according to claim 2, wherein the display image creation unit sets the assembly of half lines which pass through sampling points on line segments having the feature points as their edge points and have the barycenter of the feature points as their edge point, as the display curved surface.

11. The medical image processing device according to claim 2, wherein:
  the display unit superimposes and displays a candidate position of the display curved surface on the conversion image; and
  the display image creation unit inputs selective information on a candidate position of the display curved surface, and creates the display image based on the display curved surface defined by the selective information.

12. The medical image processing device according to claim 1, wherein the display image creation unit creates the display image based on the pixels ranging from one surface or both surfaces of the reference curved surface to the bone tissue.

13. The medical image processing device according to claim 12, wherein the display image creation unit extracts the pixels ranging from the respective pixels of the reference curved surface to the pixels which satisfy the condition of a threshold value as target pixels in the directions of both surfaces of the reference curved surface, and creates the display image using the target pixels.

14. The medical image processing device according to claim 12, wherein the display image creation unit creates the display image by defining projection lines having the respective pixels of the reference curved surface as their starting points in the direction vertical to the reference curved surface or the slice plane of the cross-sectional image, and performing shading based on the pixels on the projection lines.

15. The medical image processing device according to claim 1, wherein the display image creation unit creates a display image of a single processing target vertebral body, by calculating the reference curved surface between a first vertebral body adjacent to the processing target vertebral body and the processing target vertebral body to be set as a first border curved surface which passes through the border between the first vertebral body and the processing target vertebral body, calculating the reference curved surface between a second vertebral body facing the first vertebral body with the processing target vertebral body therebetween and the processing target vertebral body to be set as a second border curved surface which passes through the border between the second vertebral body and the processing target vertebral body, and creating the display image on the basis of the pixel group between the first border curved surface and the second border curved surface.

16. The medical image processing device according to claim 15, wherein the display image creation unit extracts, as target pixels, the pixels which satisfy the condition of a threshold value from the pixel group between the first border curved surface and the second border curved surface, and creates the display image using the processing target pixels.

17. A medical image processing method which creates a display image formed by the pixels of plural cross-sectional images, which is to be displayed on a display device for radiographic image interpretation of interosseous tissue or bone tissue, including:
    creation of a conversion image including the interosseous tissue and plural bone tissues having the interosseous tissue therebetween based on the plural cross-sectional images;
    specification of feature points by executing a process, for each conversion image, of specifying at least two points as feature points by a predetermined specifying condition using at least two conversion images having different conversion curved surfaces showing the positions of the pixels that constitute the conversion images;
    creation of a display image by calculating a reference curved surface for creating the display image on the basis of the feature points, and creating the display image on the basis of the reference curved surface; and
    display of the display image on the display device.

\* \* \* \* \*